United States Patent [19]
Brückner et al.

[11] Patent Number: 5,919,923
[45] Date of Patent: Jul. 6, 1999

[54] MESO-SUBSTITUTED TRIPYRRANE COMPOUNDS, COMPOSITIONS, AND METHODS FOR MAKING AND USING THE SAME

[76] Inventors: Christian Brückner, 1865 West 12th Avenue, Vancouver, B.C., Canada; Ross W. Boyle, 18 Paddock Way, Colchester C079HL, Essex, United Kingdom; David Dolphin, 4464 West 12th Avenue, Vancouver, B.C., Canada

[21] Appl. No.: 09/080,989

[22] Filed: May 19, 1998

Related U.S. Application Data

[63] Continuation of application No. 08/612,215, Mar. 7, 1996.

[51] Int. Cl.$^6$ .................. C07D 487/22; C07D 403/06
[52] U.S. Cl. .................. 540/145; 548/518; 548/519; 548/520; 548/521; 548/522; 548/527; 546/268.1
[58] Field of Search ............... 546/268.1, 268.4; 548/517–522; 540/145

[56] References Cited

U.S. PATENT DOCUMENTS

| | | | |
|---|---|---|---|
| 4,935,498 | 6/1990 | Sessler et al. | 540/470 |
| 5,159,065 | 10/1992 | Sessler et al. | 540/474 |
| 5,162,509 | 11/1992 | Sessler et al. | 534/15 |
| 5,182,348 | 1/1993 | Braeunling et al. | 548/527 |
| 5,302,714 | 4/1994 | Sessler et al. | 540/472 |
| 5,599,948 | 2/1997 | Wijesekera | 548/518 |
| 5,674,467 | 10/1997 | Maier et al. | 424/1.65 |
| 5,756,726 | 5/1998 | Hemmi et al. | 540/474 |

FOREIGN PATENT DOCUMENTS

WO 91/09861   7/1991   European Pat. Off.

OTHER PUBLICATIONS

Lee et al. Tetrahedron, vol. 50, No. 39 1994 pp. 11427–11440.

Bauer, V.J. et al., "Sapphyrins: Novel Aromatic Pentapyrrolic Macrocycles," *J. Am. Chem. Soc.* (1983) 105:6429–6436.

Berlin, K. et al., "New Porphyrinoid Macrocycles Containing Pyridine," *Angew. Chem. Int. Ed. Engl.* (1994) 33(2):219–220.

Berlin, K. et al., "Benziporphyrin, a Benzene–Containing, Nonaromatic Porphyrin Analogue," *Angew. Chem. Int. Ed. Engl.* (1994) 33(12):1246–1247.

Broadhurst, M.J. et al., "The Synthesis of 22 π–Electron Macrocycles. Sapphyrins and Related Compounds," *Journal of the Chemical Society* (1981) 16:2111–2116.

Cavaleiro, J.A.S. et al., "An Anomalous Dipyrrole Product from Attempted Synthesis of a Tetraarylporphyrin," *J. Org. Chem.* (1988) 53:5847–5849.

Charriere, R. et al., "The Chemistry of Polyphrins 2.$^1$ Synthesis of Hexaphyrins and Their Metal Complexes," *Heterocycles* (1993) 36(7):1561–1575.

Chmielewski, P.J. et al., "Tetra–p–tolylporphyrin with an Inverted Pyrrole Ring: A Novel Isomer of Porphyrin" *Angew. Chem. Int. Ed. Engl.* (1994) 33(7):779–781.

Chmielewski, P.J. et al., "5,10,15,20–Tetraphenylsapphyrin—Identification of a Pentapyrrolic Expanded Porphyrin in the Rothemund Synthesis," *Chem. Eur. J.* (1995) 1(1):68–73.

Furuta, H. et al., "'N–Confused Porphyrin': A New Isomer of Tetraphenylporphyrin," *J. Am. Chem. Soc.* (1994) 116:767–768.

Hill, C.L. et al., "Isolation and Characterization of the Principal Kinetic Product in the Preparation of a Sterically Hindered Tetra–arylporphyrin: X–Ray Structure of a Bis-(dipyrromethene) Complex of Zinc, $Zn^{11}(C_{22}H_{13}Cl_4N_2)_2$•toluene" *J. Chem. Soc., Chem. Commun.* (1985):1228–1229.

(List continued on next page.)

Primary Examiner—Mukund J. Shah
Assistant Examiner—Pavanaram K. Sripada
Attorney, Agent, or Firm—Morrison & Foerster, LLP

[57] ABSTRACT

The invention provides for tripyrrane compounds of the formula

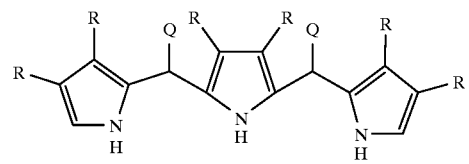

wherein:

each Q represents, typically, an alkyl group, cycloalkyl group, aryl group, or a heteroaryl group; and each R represents hydrogen, an alkyl group, alcohol group, or a carbonyl-containing group. Additionally, there are described methods to prepare such compounds, for example, comprising the steps of:

(a) reacting a compound of the formula:

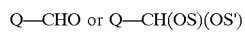

wherein S and S' are independently lower alkyl, an aryl group containing from 5 to 14 ring atoms, and $-(CH_2)_n-$ where n=2–4;

with a stoichiometric excess of a pyrrole having the formula:

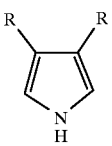

in the presence of a catalytic amount of an acid;

(b) removing the unreacted pyrrole or any other solvents used in (a) by evaporation to form a residue; and (c) treating the residue to remove high molecular weight polymeric materials and the corresponding dipyrromethane by-product, leaving the desired compound.

24 Claims, 4 Drawing Sheets

OTHER PUBLICATIONS

Lee, C–H. et al., "One–Flask Synthesis of Meso–Substituted Dipyrromethanes and Their Application in the Synthesis of Trans–Substituted Porphyrin Building Blocks," *Tetrahedron* (1994) 50(39):11427–11440.

Rexhausen, H. et al., "The Synthesis of a New 22 π–Electron Macrocycle: Pentaphyrin," *J. Chem. Soc., Chem. Commun.* (1983):275.

Sessler, J.L. et al., "Sapphyrins and Heterosapphyrins," *Tetrahedron* (1992) 48(44):9661–9672.

Sessler, J.L. et al., "Synthesis and Crystal Structure of a Novel Tripyrrane–Containing Porphyrinogen–like Macrocycle," *J. Org. Chem.* (1987) 52:4394–4397.

Sessler, J.L. et al., "Texaphyrins: Synthesis and Applications," *Acc. Chem. Res.* (1994) 27:43–50.

Sessler, J.L. et al., "A Nonaromatic Expanded Porphyrin Derived from Anthracene—A macrocycle which Unexpectedly Binds Anions," *Angew. Chem. Int. Ed. Engl.* (1992) 31(4):452–455.

Shipps, G., Jr. et al., "New Synthetic Receptors Derived from Porphyrins," *Tetrahedron Letters* (1994) 35(37):6823–6826.

S. Vigmond et al., "Direct Synthesis of Aryldipyrromethanes," *Tetrahedron Letters*, vol. 35, pp. 2455–2458, 1994.

P–Y. Heo et al., "Facile Syntheses of Modified Tripyrranes and Their Application to the Syntheses of Regioisomerically Pure Porphyrin Derivatives," *Bulletin of the Korean Chemical Society*, 17, pp. 515–521 1996.

*Chemical Abstracts*, vol. 125, No. 11 (1996), Abstract No. 142406.

Tetrahedron Letter, vol. 37(2), pp. 197–200, "Stepwise Synthesis of Core–Modified, Meso–Substituted Porphyrins".

Tetrahedron Letter, vol. 35(16), pp. 2455–2458, "Direct Synthesis of Aryldipyrromethanes".

Thomas Carrell, "Modellverbinungen zur Untersuchung der Primäprozesse in der Photosynthese" Doctoral Disseration, Ruprecht–Karls Universisität, Heidelberg, Germany, 1992.

Sessler et al, Chem. Eur. J., vol. 1, No. 1, 1995, pp. 56–67.

Broadhurst et al, J.C.S. Perkin, I pages 2111–2116 (1972).

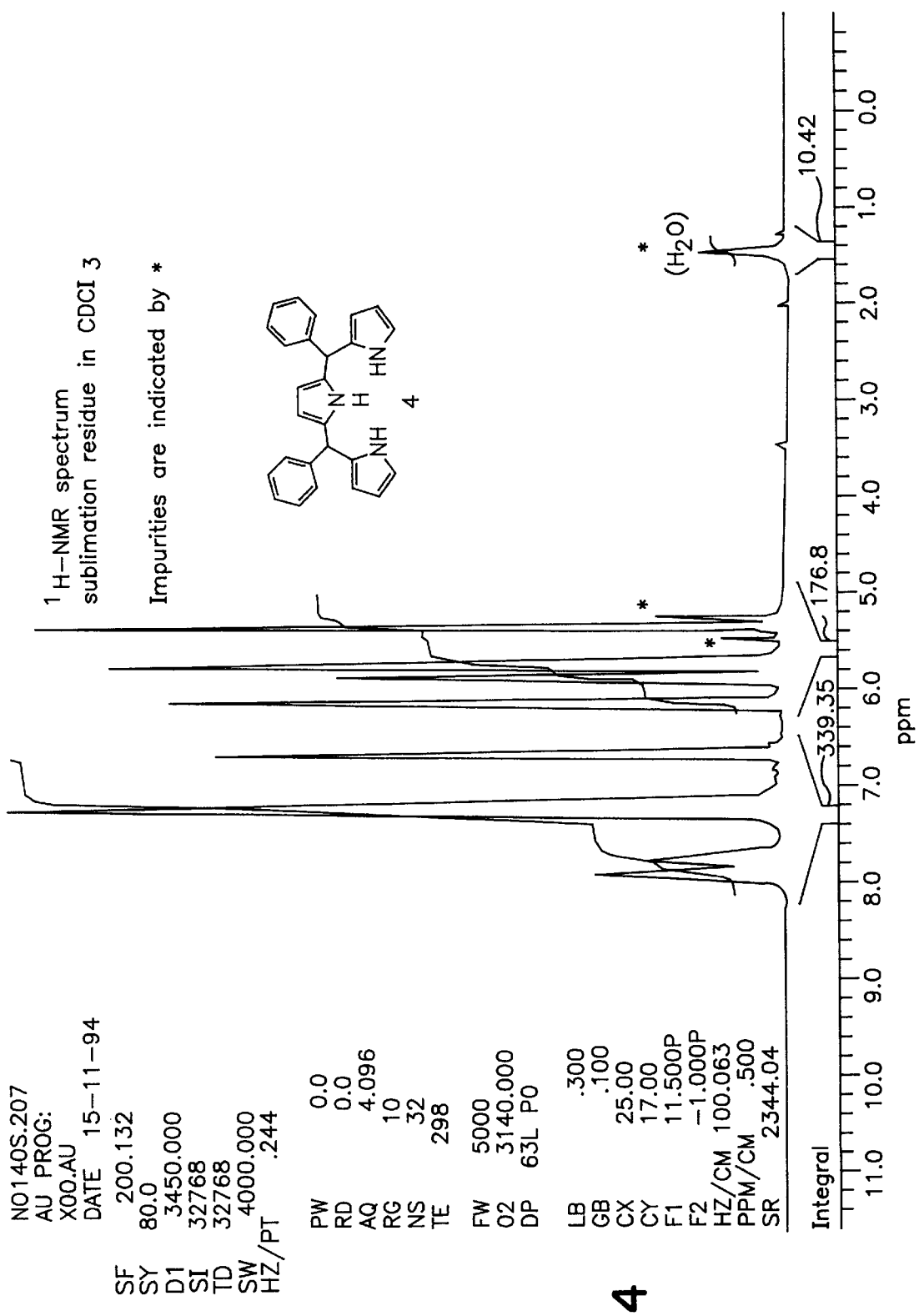

MESO-SUBSTITUTED TRIPYRRANE COMPOUNDS, COMPOSITIONS, AND METHODS FOR MAKING AND USING THE SAME

The present application is a continuation of U.S. Ser. No. 08/612,215, filed Mar. 7, 1996, an allowed application, the complete text and figures of which are hereby incorporated by reference as if fully set forth.

BACKGROUND OF THE INVENTION

1. Field of the Invention

The present invention relates to certain meso-substituted tripyrrane compounds, compositions containing them, their preparation, and their use as key intermediates in synthesizing 5,10-disubstituted porphyrin compounds or other 5,10-disubstituted polypyrrolic macrocycles. In particular, the invention relates to the use of a one-step synthesis of meso-substituted tripyrranes, which offers considerable advantages with respect to the large scale, industrial production of meso-substituted porphyrins and other polypyrrolic macrocycles. Many of the meso-substituted porphyrins and polypyrrolic macrocycles made in this way are useful as:

- photosensitizers for photodynamic therapy;
- chelators for radionuclides;
- MRI contrast agents (i.e., chelators for paramagnetic metals);
- other biomedical uses; and
- technical uses for infrared absorbing dyes, such as imaging, data recording and printing.

2. Description of the Related Art

β-alkyl substituted tripyrrane compounds have been recognized as important building blocks for synthesizing a wide variety of polypyrrolic macrocyclic systems. For example, in 1972, Broadhurst et al. condensed a bis(pyrrolylmethyl) pyrrole diacid with a similar two-ring component, specifically, a β-alkyl dipyrrin dialdehyde, to form a 22 π-electron macrocycle containing five pyrrolic rings, which was named "sapphyrin." Broadhurst et al., "The Synthesis of 22 π-Electron Macrocycles. Sapphyrins and Related Compounds", *J.C.S. Perkin I*, 2111–16 at 2112 (1972). Other workers made further contributions along the same lines, as follows:

| Year Reported | Description | Source |
|---|---|---|
| 1983 | Condensed a β-alkyl tripyrrane dialdehyde with a dipyrrylmethane to produce a pentaphyrin. | Rexhausen et al., "Synthesis of a New 22 π-Electron Macrocycle: Pentaphyrin", J. Chem. Soc., Chem. Commun., 275. |
| 1983 | Coupled a bipyrroledicarboxaldehyde with a β-alkyl tripyrrane diacid to synthesize decamethylsapphyrin. | Bauer et al., "Sapphyrins: Novel Aromatic Pentapyrrolic Macrocycles", J. Am. Chem. Soc., 105, 6429–36 at 6431. |
| 1987 | Used an acid-catalyzed 1:1 Schiff base condensation of o-phenylenediamine or 1,4-diaminobutane with a β-alkyl diformyltripyrrane to form a macrocycle having saturated methylene bridges to link the pyrrole subunits. | Sessler et al., "Synthesis and Crystal Structure of a Novel Tripyrrane-Containing Porphyrinogen-like Macrocycle", J. Org. Chem., 52, 4394–97 at 4395. |
| 1990 and 1992 | Condensed an α-dicarboxyaldehyde, β-alkyl tripyrrane with o-phenylenediamine to form an expanded porphyrin known as a "texaphyrin." | Sessler et al., U.S. Pat. Nos. 4,935,498 and 5,162,509 (See FIG. 26). |
| 1992 | Condensed a β-alkyl dicarboxylic acid tripyrrane with a diformyl bipyrrole under acidic conditions in the presence of oxygen to give a decaalkylsapphyrin. | Sessler et al., "Sapphyrins and Heterosapphyrins", Tetrahedron, 48:44, 9661–72 at 9663. |
| 1992 | Performed an acid-catalyzed 1:1 condensation of 1,8-diaminoanthracene and a β-alkyl diformyl tripyrrane to form an expanded porphyrin. | Sessler et al., "A Nonaromatic Expanded Porphyrin Derived from Anthracene -- A Macrocycle Which Unexpectedly Binds Anions", Angew. Chem. Int. Ed. Engl., 31:4, 452–55 at 453. |
| 1992 and 1994 | Condensed 4,4'-diethyl-5,5'-diformyl-3,3'-dimethyl-2,2'-bipyrrole and 2,5-bis(5-carboxy-3-ethyl-4-methyl-pyrrol-2-ylmethyl)-3,4-diethylpyrrole to produce 3,8,12,13,17,22-hexaethyl-2,7,18,23-tetramethyl-sapphyrin. | Sessler et al., U.S. Pat. Nos. 5,302,714 (FIGS. 1C and 5D) and 5,159,065. |
| 1993 | Reacted a β-alkyl tripyrrane dialdehyde with the corresponding α,α'-unsubstituted tripyrrane to afford, after oxidation with iodine and p-benzoquinone, a β-peralkyl-hexaphyrin. | Charriere et al., "The Chemistry of Polyphyrins 2, Synthesis of Hexaphyrins and their Metal Complexes", Heterocycles, 36:7, 1561–75 at 1562. |
| 1994 | Condensed pyridine-2,6-dicarbaldehyde with a β-alkyl tripyrranedicarboxylic acid, followed by oxidation to form an 18-π macrocycle called "pyriporphin." | Berlin et al., "New Porphyrinoid Macrocycles Containing Pyridine", Angew. Chem. Int. Ed. Engl., 33:2, 219–20 at 219. |
| 1994 | Decarboxylated a β-alkyl tripyrrane-dicarboxylic acid, condensed it with | Berlin et al., "Benziporphyin, a Benzene-Containing Nonaromatic |

-continued

| Year Reported | Description | Source |
| --- | --- | --- |
| | isophthaladehyde, and oxidized the product in situ with p-chloranil to give a benzene-containing macrocycle called "benziporphin." | Porphyrin Analogue", Angew. Chem. Int. Ed. Engl., 33:12, 1246–47 at 1246. |
| 1994 | Performed a Schiff base condensation between a β-alkyl diformyltripyrrane and an aromatic 1,2-diamine, such as o-phenylene-diamine derivative, to form an expanded porphyrin called a "texaphyrin." | Sessler et al., "Texaphyrins: Synthesis and Applications", Acc. Chem. Res., 27, 43–50 at 46. |

However, the syntheses of the β-alkyl tripyrranes used above as starting materials are generally lengthy and involve several reaction steps. Specifically, when the syntheses of β-alkyl tripyrranes are described, they typically involve: (1) the reaction of an α-free, α'-ester-β-tetraalkyl dipyrromethane and an α-ester, α'-carboxaldehyde-β-dialkylpyrrole and subsequent reduction of the dipyrromethene moiety first formed (e.g., see Bauer et al. at 6431 and 6435) or (2) the reaction of an α-acetoxymethyl-α'-ester-β-dialkylpyrrole with an α,α'-free β-dialkylpyrrole, subsequent removal of the esters, and diformylation, if required (e.g., see Sessler et al., *J. Org. Chem.*, 52 at 4395; U.S. Pat. Nos. 4,935,498, 5,162,509, 5,159,065 and 5,302, 714; Sessler et al. *Tetrahedron*, 48:44 at 9661–63; Charriere et al., *Heterocycles*, 36:7 at 1567; and Seseler et al., *Acc. Chem. Res.*, 27 at 45). The pyrrolic starting materials themselves must also be synthesized from simpler compounds, which involves several more reaction steps.

One group of workers has disclosed the reaction at room temperature of an aldehyde, such as benzaldehyde, with an excess amount of pyrrole in the absence of a solvent to produce, primarily, a meso-substituted dipyrromethane, which is used as a key building block in the synthesis of linear porphyrin arrays. Lee et al., "One-Flask Synthesis of Meso-Substituted Dipyrromethanes and Their Application in the Synthesis of Trans-Substituted Porphyrin Building Blocks", *Tetrahedron*, 50:39, 11427–40 (1994). Thin layer chromatography ("TLC") analysis of the reaction mixture showed, in addition to the dipyrromethane product, "a tiny amount (<5%) of a tailing component." Lee et al. attempted to isolate the tailing component and "provisionally" assigned it the structure of "the corresponding tripyrromethane" based on NMR spectroscopy. However, this compound was described as being less stable than the dipyrromethane primary product and as changing "from a white solid to a black material over one day at room temperature." Lee et al. at 11429. No further efforts were made to isolate or confirm the identity of the impurity speculated to be a "tripyrromethane", and no teachings are provided by Lee et al. with respect to how to make and use the meso-substituted tripyrranes of the invention. Rather, the focus of Lee et al. is on the dipyrromethane as the desired product of the reaction, as opposed to the tripyrrane.

Rebek et al., *J. Tetrahedron Lett.*, 35, 6823 (1994) mention briefly in the reference section of their paper a preparation for meso-phenyldipyrromethane by reacting benzaldehyde and pyrrole in the solvent toluene and in the presence of an acid catalyst, a procedure originating from a Ph.D. thesis (T. Carell, Ph.D. thesis, Ruprechts-Karl-Universitat Heidelberg (1994)). However, the production or other occurrence of any tripyrrane was not disclosed.

When others have tried to react a benzaldehyde directly with pyrrole, they have usually obtained either an inverted meso-tetraphenylporphyrin compound (specifically, 2-aza-21-carba-5,10,15,20-tetraphenylporphyrin, also known by the trivial name "N-confused porphyrin") or a mixture of the inverted tetraphenylporphyrin, non-inverted tetraphenylporphyrin, and sapphyrin. See Furuta et al., "'N-Confused Porphyrin': A New Isomer of Tetraphenylporphyrin", *J. Am. Chem. Soc.*, 116, 767–68 (1994); Chmielewski et al., "Tetra-p-tolylporphyrin with an Inverted Pyrrole Ring: A Novel Isomer of Porphyrin", *Angew. Chem. Int. Ed. Engl.*, 33:7, 779–81 (1994); and Chmielewski et al., "5,10,15,20-Tetraphenylsapphyrin—Identification of a Pentapyrrolic Expanded Porphyrin in the Rothemund Synthesis", *Chem. Eur. J.*, 1:1, 68–73 (1995). A dibenzofuranyl pyrromethane resulted when o-acetoxybenzaldehyde was heated with pyrrole in hot acetic acid. Cavaleiro et al., "An Anomalous Dipyrrole Product from Attempted Synthesis of a Tetra-arylporphyrin," *J. Org. Chem.*, 53:5847–49 (1988). When pyrrole is reacted with 2,6-dichlorobenzaldehyde and zinc acetate, the solid phase of the reaction mixture was said to contain the desired porphyrin complex, tetrakis(2,6-dichlorophenyl)porphirato zinc(II), and the liquid phase was said to contain another product, bis[(meso-2,6-dichlorophenyl)-5-(o,o'-dichlorobenzyl)dipyrromethene] zinc(II). Hill et al., "Isolation and Characterization of the Principal Kinetic Product in the Preparation of a Sterically Hindered Tetra-Arylporphyrin: X-ray Structure of a Bis(dipyrromethene) Complex of Zinc, $Zn^{II}(C_{22}H_{13}Cl_4N_2)_2$·toluene," *J. Chem, Soc. Chem. Commun.*, 1228–29 (1985).

It has now been found that meso-substituted tripyrranes can be made in what is virtually a one-step synthesis, sometimes even without requiring the chromatographic separations usually necessary to purify polypyrrolic materials. This means that the subsequent synthesis of polypyrrolic macrocycles can be greatly simplified. Using the compounds and methods of the invention, a macrocycle such as meso-diphenylpentaphyrin, for example, can be prepared in just three steps, as compared with the 10–12 steps needed for the meso-unsubstituted, β-alkylated analogue, beginning with simple pyrrolic compounds and benzaldehyde as starting materials.

Further, meso-substituted macrocycles, such as pentapyrrolic macrocycles, exhibit considerably altered spectroscopic behavior as compared with the meso-unsubstituted, β-alkyl counterparts, due at least in part to the different site of substitution (β only vs. meso and, optionally, also β). When the meso-substituent is aryl or heteroaryl, for example, it also confers significantly different electronic properties. Further still, the addition of a large, fairly rigid and flat substituents such as aryl groups changes the steric requirements of the molecule. This alters the biological properties of meso-substituted macrocycles, as compared with their beta-alkyl analogs.

More importantly, the meso-substituents of the compounds of the invention also provide a way to manipulate the biodistribution and pharmacokinetics of the polypyrrolic macrocycles made from the compounds of the invention by changing the peripheral substitution patterns. Specifically, the most active photosensitizers used in photodynamic therapy are typically highly amphiphilic in nature. If the meso-substituents on the tripyrrane compounds of the invention are phenyl groups, for example, this presents an opportunity to introduce substituents on the phenyl groups to fine-tune the amphiphilicity, the spectroscopic properties, and/or the metal binding properties, of the resulting macrocycle even further.

To optimize the biological properties of any compound, it is of great advantage to be able to prepare whole "libraries" of related compounds. The alkyl- or aryl-substituents of the tripyrranes of the invention can be easily reacted with other monocyclic or polycyclic compounds to synthesize 5,10-disubstituted polypyrrolic macrocycles, giving access to macrocycles of an almost unlimited variety. Further, these ends are accomplished in only a few synthetic steps and, potentially, on a large scale.

Thus, the processes of the invention provide efficient methods for producing libraries of compounds having flexible, "fine-tuned" biological activity, such as precisely delivered photosensitizing ability in standard photodynamic therapy protocols.

SUMMARY OF THE INVENTION

According to the present invention, there have been prepared novel meso-substituted tripyrrane compounds of Formula I:

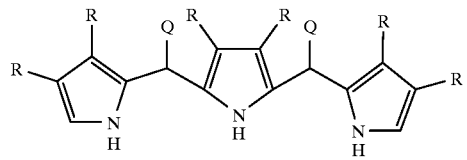

wherein:

Q is an alkyl group, a cycloalkyl group having from 5 to 7 ring atoms, or an aryl or heteroaryl group having from 5 to 12 ring atoms and all R groups are identical hydrogen, alkyl, alcohol, or carbonyl-containing groups.

The invention also concerns compositions comprising:

(a) from 5 to 100 mole % by weight of a compound of Formula I; and (b) from 0 to 95 mole % by weight of the dipyrromethane corresponding to the compound of Formula I.

Further, a method has been found for efficiently synthesizing the compounds of Formula I. Specifically, in the invention, a method for making the compound having Formula I comprises the steps of:

(a) reacting a compound of the formula:

Q—CHO or Q—CH(OS)(OS')

wherein Q is as defined above, and

S and S' are independently lower alkyl, an aryl group containing from 5 to 14 ring atoms, and —(CH$_2$)$_n$— where n=2–4;

with a stoichiometric excess of a pyrrole having the formula:

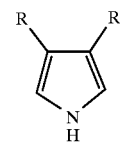

in the presence of a catalytic amount of a strong Lewis or Bronsted acid;

(b) removing the unreacted pyrrole or any other solvents used in (a) by evaporation to form a residue;

(c) treating the residue to remove high molecular weight polymeric materials and the corresponding dipyrromethane by-product, leaving the compound of Formula I.

Further, the invention provides processes for making 5,10-disubstituted porphyrin compounds or other 5,10-disubstituted polypyrrolic macrocycles. By "5,10-disubstituted polypyrrolic macrocycle" is meant a polypyrrolic macrocycle having at least two meso-substituents at neighboring meso-positions of the macrocycle. The term is intended to include polypyrrolic macrocycles having more than two meso-substituents, such as, for example, 5,10,15,20-tetraphenylsapphyrin.

One process comprises the steps of:

(a) cyclizing, in the presence of an acid catalyst, a compound of Formula I having two terminal pyrrole rings, each with an unsubstituted α-position:

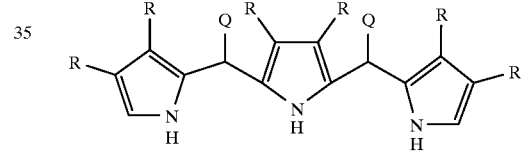

wherein:

Q represents identical alkyl groups, cycloalkyl groups having from 5 to 7 ring atoms, or aryl or heteroaryl groups having from 5 to 12 ring atoms and R represents identical hydrogen, alkyl, alcohol or carbonyl-containing groups;

with a compound having a formula selected from the group consisting of:

Q—CHO, Q—CH(OS)(OS'),

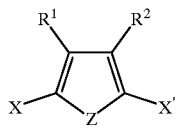 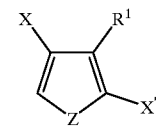

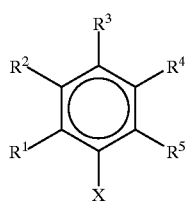 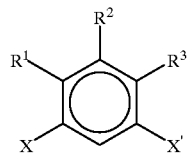

-continued

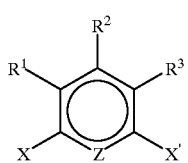

and

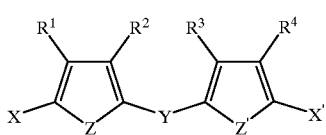

wherein:
S and S' are independently lower alkyl, an aryl group containing from 5 to 14 ring atoms, and —(CH$_2$)$_n$— where n=2–4;

R$^1$–R$^5$ are independently hydrogen, lower alkyl, alcohol or carbonyl-containing groups;

X and X' are groups capable of coupling with the unsubstituted α-positions of the terminal pyrrole rings of the compound of Formula I;

Z and Z' are independently —N—, >NH, —O— or a bivalent sulfur atom; and

Y is a direct link, alkylene, pyrrolylene, furanylene, phenylene, thiophenylene, benzylene, or alkylene-pyrrolene-alkylene, to form a cyclized intermediate; and (b) oxidizing the cyclized intermediate to form the corresponding 5,10-disubstituted porphyrin compound or other 5,10-disubstituted polypyrrolic macrocycle.

A second process for making a 5,10-disubstituted porphyrin compound or other 5,10-disubstituted polypyrrolic macrocycle comprises the steps of:

(a) cyclizing, in the presence of an acid catalyst, a compound of Formula II:

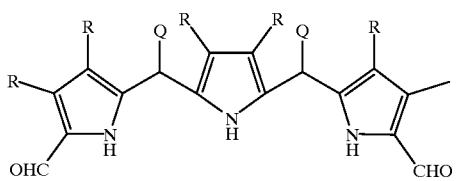

wherein:
Q represents identical alkyl groups, cycloalkyl groups having from 5 to 7 ring atoms, or aryl or heteroaryl groups having from 5 to 12 ring atoms and R represents identical hydrogen, alkyl, alcohol or carbonyl-containing groups;

with either (i) a planar cyclic co-reactant having a formula selected from the group consisting of:

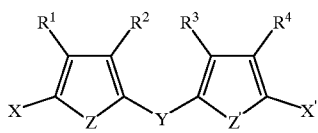

and

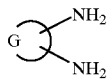

wherein:
R$^1$–R$^4$ are independently hydrogen, lower alkyl, alcohol, or carbonyl-containing groups;

Z and Z' are each —N—, >NH, —O— or —S—;

Y is a direct link, alkylene, pyrrolylene, furanylene, phenylene, thiophenylene, benzylene, or alkylene-pyrrolene-alkylene;

X and X' are independently hydrogen or —COOH; and

G represents the atoms necessary to complete a carbocyclic or heterocyclic ring having from 5 to 14 ring atoms, or (ii) a compound of Formula I:

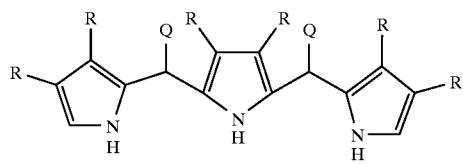

to form a cyclized intermediate; and (b) oxidizing said cyclized intermediate to form the corresponding 5,10-disubstituted porphyrin compound or other 5,10-disubstituted polypyrrolic macrocycle.

BRIEF DESCRIPTION OF THE DRAWINGS

The present invention will be more clearly understood by referring to the following drawings, in which:

FIG. 4 shows the $^1$H-NMR spectrum of a sublimation residue containing 5,10-diphenyltripyrrane in CDCl$_3$.

DETAILED DESCRIPTION OF THE INVENTION

Figure 1:
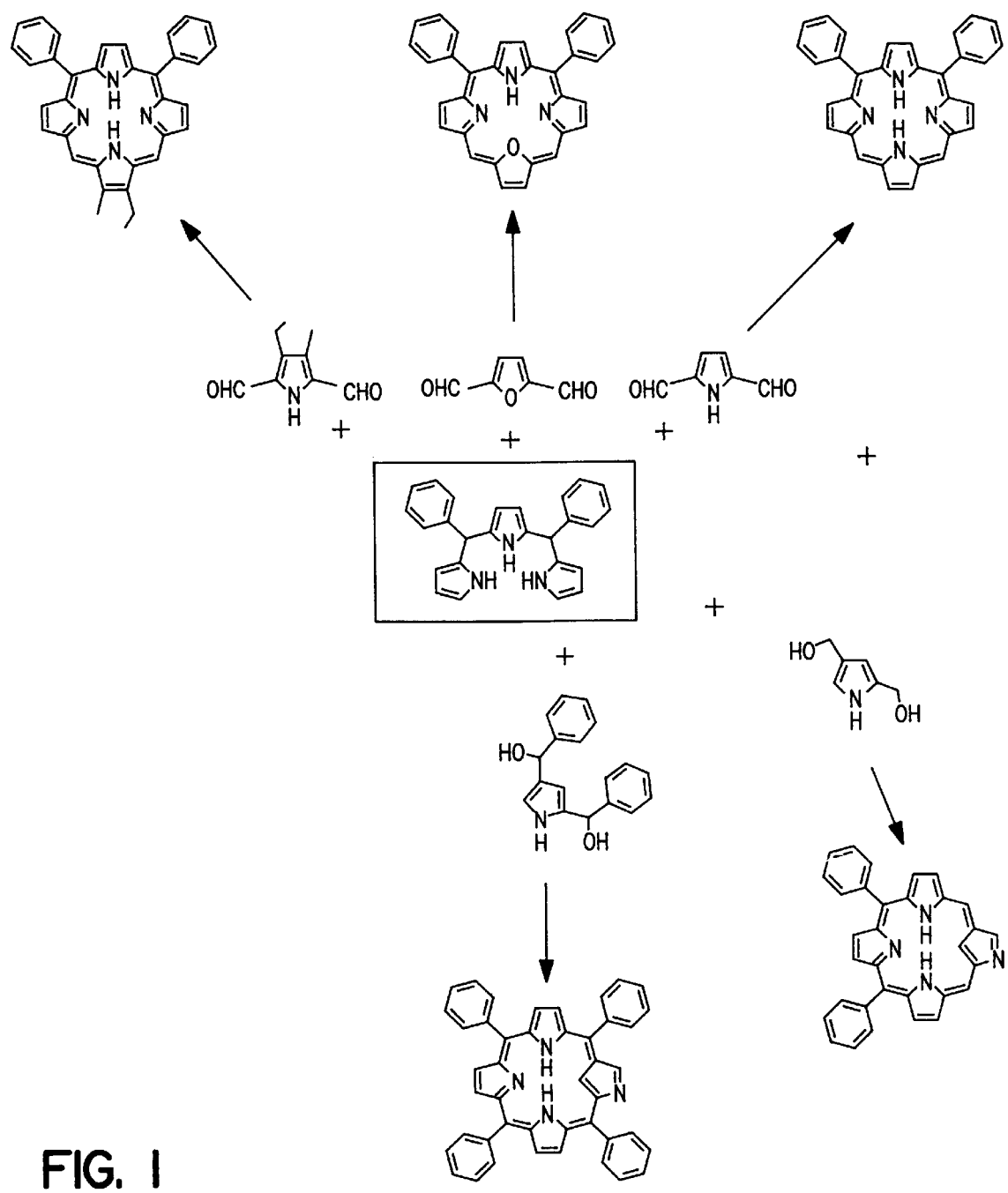
FIG. 1 shows the formation of a number of tetrapyrrolic compounds.

The meso-disubstituted tripyrrane compounds of the invention have Formula I, as described and shown above. Q in Formula I can be any one of a large number of alkyl groups, substituted or unsubstituted cycloalkyl groups, substituted aromatic rings or substituted or unsubstituted heterocyclic rings, but should be chosen to have no adverse effect on the ability of the compound of Formula I to undergo the cyclization and oxidation reactins used to prepare the polypyrrolic macrocycles of the invention.

When Q in Formula I is an alkyl group, it preferably has from about 1 to about 18 carbon atoms, more preferably about 1 to 12 carbon atoms and, even more preferably, from about 1 to 6 carbon atoms. Examples of useful alkyl groups are methyl, ethyl, isopropyl, sec-butyl, tert-butyl, n-pentyl and n-octyl.

When Q is a cycloalkyl group, it preferably contains from about 5 to 7 carbon atoms. Examples of typical cycloalkyl groups include cyclopropyl, cyclohexyl and cycloheteroalkyl, such as glucopyranose or fructofuranose sugars. When Q is a cycloalkyl group, it may be unsubstituted or substituted with any group that does not interfere with the reaction step (a), such as an aldehyde group, an acetal, or any other acid-labile group.

When Q is an aryl group, Q typically contains from about 5 to about 14 carbon atoms, preferably about 5 to 12 carbon atoms and, optionally, can contain one or more rings that are fused to the existing conjugated pyrrolic ring structure. Examples of particularly suitable aromatic rings include phenyl, naphthyl, anthracenyl, phenanthrenyl, and the like.

When Q is a heteroaryl group, Q typically contains from about 5 to 14 ring atoms, preferably about 5 to 12 ring atoms, and one or more heteroatoms. Examples of suitable heteroaryl groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3,-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,4-oxazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 1,2-benzodiazine, 1,3-benzodiazine, naphthyridine, pyrido[3,4-b)-pyridine, pyrido(3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when Q is a heteroaryl group, it is selected from the group consisting of furan, pyridine, N-alkylpyridine, 1,2,3- and 1,2,4-triazoles, indene, anthracene and purine.

Preferably, Q is a phenyl or pyridinyl group substituted with one or more non-interfering substituents having from 1 to 6 carbon atoms. Even more preferably, Q is a phenyl or pyridinyl group having the formula:

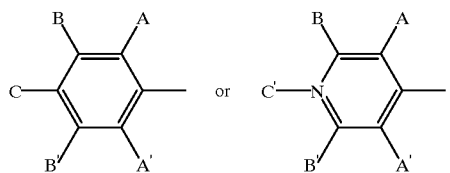

where A, A', B, B', C and C' can be any one of a large number of substituents that are generally used to "fine tune" the biological activity, biodistribution, solubility, absorption, clearance characteristics, and/or physical properties of the desired product. Preferably, substituents are selected in such a manner that the polypyrrolic macrocyclic compound to be made from the tripyrrane of Formula I will be an amphiphilic molecule. By "amphiphilic" is meant that the molecule has become more asymmetric, such as (1) having both (a) a highly polar water-soluble region and (b) a highly hydrophobic, water-insoluble region;

(2) having both (a) a non-ionic region and (b) an ionic region; or (3) having both (a) an anionic portion and (b) a cationic portion.

Preferably, A, A', B, B', C and C' are independently hydrogen, halogen, lower alkyl, lower alkoxy, hydroxy, carboxylic acid, cyano, nitro, or the like. Most preferably, Q is a phenyl group that is either unsubstituted or substituted with a halogen atom.

R in Formula I can be any substituent that does not deactivate the pyrrole starting material in the synthesis of a compound of Formula I. For example, electron-withdrawing groups such as halogens and directly linked oxygen should usually be avoided in this position. Preferably, R is selected from the group consisting of hydrogen; lower alkyl such as methyl, ethyl, n-propyl, i-propyl, n-butyl, and tert-butyl; alcohols such as —$CH_2OH$ and —$(CH_2)_3OH$; carboxyl groups such as —$CH_2C(O)$ $CH_3$, —$(CH_2)_2COOH$, —$(CH_2)_2COOCH_3$, and —$(CH_2)_2COOC_2H_5$; and amides of the formula —CO—NR'R" where R' and R" are independently hydrogen, alkyl or aryl. In a particularly preferred embodiment, R is either hydrogen or a lower alkyl group. Further, it is preferred that all R groups should be the same to prevent any confusion with regioisomers, unless the substituents confer the same regiochemical selectivity on the outcome of the condensation.

The meso-disubstituted tripyrrane compound of Formula I is preferably made by:

(a) reacting a compound of the formula:

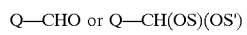

Q—CHO or Q—CH(OS)(OS')

wherein Q, S and S' are as defined above, with a stoichiometric excess of a pyrrole having the formula:

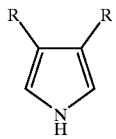

in the presence of a catalytic amount of a strong Lewis or Bronsted acid;

(b) removing the unreacted pyrrole and any other solvent used in step (a) by evaporation to form a residue;

(c) treating the residue to remove polymeric materials; and (d) removing the corresponding dipyrromethane by-product from the residue of step (c), leaving the compound of Formula I.

In the formula:

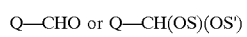

Q—CHO or Q—CH(OS)(OS')

S and S' can be can be any one of a large number of substituents. Preferably, S and S' are independently lower alkyl, such as methyl, ethyl, i-propyl, t-butyl and n-pentyl; an aryl group containing from 5 to 14 ring atoms, such as phenyl, naphthyl, pyridinyl, amidazolyl, furanyl, and the like; and —$(CH_2)_n$— where n is 2, 3 or 4.

In the process of making the compound of Formula I, the molar ratio of the compound having the formula

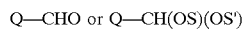

Q—CHO or Q—CH(OS)(OS')

and the pyrrole starting material can vary greatly between the ranges of about 2:3 to about 1:40, depending upon the solubility and reactivity of the reactants and products. Preferably, however, if the pyrrole is not substituted in the β-position, i.e., both R groups are hydrogens, an excess amount of the pyrrole is used as the solvent and is, therefore, present in a much greater molar quantity than the compound Q—CHO or Q—CH(OS)(OS'). On the other hand, if the pyrrole has β-substituents (other than hydrogen), the use of another solvent, in addition to the pyrrole, is preferred, and the relative amount of the pyrrole will tend to be lower, i.e., from about 2:3 to about 1:10. Thus, an excess amount of the pyrrole starting material can be used as the solvent, and this is particularly preferred where both R groups on the pyrrole molecule are hydrogens. However, an organic solvent other than the pyrrole can also be used in combination with the excess amount of the pyrrole present to form a mixed solvent, and this is particularly preferred where both R groups are not hydrogen.

When a solvent in addition to the pyrrole starting material is used, it can be any one of a wide variety of organic solvents that is capable of dissolving at least one of the reactants and, yet, does not interfere with the course of the reaction to any significant degree. Preferably, such a solvent should also have a boiling point sufficiently low to evaporate off with the excess pyrrole present in the evaporation step (b). Examples of such solvents include alcohols, such as methanol, ethanol, i-propanol, n-butanol, 2-ethylhexanol, benzyl alcohol, and glycerol; ethers such as diethyl ether, n-butyl ether and dimethoxyethane; aromatic solvents, such as benzene, toluene, and aniline; ketones such as acetone and methyl ethyl ketone; esters such as ethyl acetate, butyl acetate, and ethyl benzoate; and chlorinated solvents such as carbon tetrachloride, chloroform, dichloromethane, and 1,1,1-trichloroethane.

The strong Lewis or Bronsted acid of step (a) is generally used in only catalytic amounts. Particularly suitable strong Lewis or Bronsted acids include mineral acids such as hydrobromic acid (HBr), hydrochloric acid (HCl), and sulfuric acid ($H_2SO_4$); organic acids such as acetic acid; halogenated acids such as boron trifluoride etherate ($BF_3Et_2O$), trichloroacetic acid ($CCl_3COOH$), trifluoroacetic acid ($CF_3COOH$), and triflic acid ($CF_3SO_3H$); and sulfonic acids such as benzenesulfonic acid and p-toluenesulfonic acid. Solid-phase, bound acids such as cation exchange resins and other polymeric acids or clays, such as montmorillonite, may also be suitable strong acids to catalyze the reaction. In a particularly preferred embodiment, the strong Lewis or Bronsted acid of step (a) is either p-toluenesulfonic acid or trifluoroacetic acid.

In a preferred embodiment, the reaction takes place under an inert atmosphere to avoid oxidation or oxidative polymerization of the components. When used, the inert atmosphere is usually provided by forming a protective blanket of an inert gas, such as argon, helium, or $N_2$, over the reaction mixture or bubbling an inert gas through it. Other methods of providing an inert atmosphere include performing the reaction under reduced pressure to form an atmosphere of solvent vapor(s).

The reaction temperature in step (a) can vary widely depending on the reactivity of the reactants. However, the temperature should not be so high as to decompose the reactants or so low as to cause inhibition of the condensation or freezing of the solvent. In most cases, the reaction in step (a) can take place at a temperature ranging from about room temperature, for reasons of convenience, to the reflux temperature of the reaction mixture, which typically varies from about 25 to about 150° C.

The time required for the reaction of the Q—CHO or Q—CH(OS)(OS') compound and the above-described pyrrole starting material will depend to a large extent on the temperature being used and the relative reactivities of the starting materials. Particularly when the meso-substituents are aryl, cycloalkyl, or a bulky alkyl group such as tert-butyl, the time required for the reaction may increase due to steric hindrance. Therefore, the reaction time can vary greatly, for example, from about five minutes to about two days. Typically, the time required for the formation of the compound of Formula I is in the range of about five minutes to two hours, preferably, about 15 minutes. Various known techniques such as different types of chromatography, especially thin layer chromatography (TLC), gas chromatography (GC), or optical spectroscopy can be used to follow the progress of the reaction by the disappearance of the starting Q—CHO or Q—CH(OS)(OS') compound.

In step (b) of the process of making the compound of Formula I, in accordance with the invention, the unreacted portion of the pyrrole is removed by evaporation to leave a residue containing the product. Preferably, this removal step by evaporation takes place under reduced pressure to increase the rate of evaporation and to reduce the temperature necessary to evaporate off substantially all of the unreacted pyrrole.

At the conclusion of the evaporation step (b), a residue remains, from which the meso-disubstituted tripyrrane can be isolated by any conventional means, such as by chromatography, crystallization, re-crystallization, sublimation, various combinations of these methods, and the like. Typically, two primary types of impurities must be removed from the residue: (1) high molecular weight polymeric materials; and (2) the dipyrromethane molecule corresponding to the desired tripyrrane product, which occurs as a by-product of the above-described reaction.

Preferably, the isolation step (c) comprises a combination of two steps—one to remove each major impurity. To remove the polymeric materials, any conventional means may be used. The removal of polymeric material is preferred, at least to some extent, to increase the ease and/or rate of removal of the dipyrromethane by-product and to improve overally product purity. However, after the evaporation step (b), it is possible to remove the dipyrromethane by-product without requiring a separate step to remove polymeric materials.

When these materials are removed from the residue, typically, the removal is accomplished chromatographically. Preferably, a column of silica or alumina is used. Any eluting solvent that provides good separation on the column of choice may be used. Examples of particularly useful eluting solvents include chlorinated solvents such as chloroform, carbon tetrachloride, mixtures thereof and the like.

As to removal of the dipyrromethane by-product, any suitable and effective means may be employed. However, sublimation is the preferred method. If sublimation is to be used to remove the dipyrromethane by-product, the residue of step (b), which typically contains the compound of Formula I and the corresponding dipyrromethane by-product, is slowly heated (usually at a rate of about 0.1 to about 2.0° C./minute, preferably about 0.50 to about 1.00° C./minute) until the sublimation temperature of the dipyrromethane by-product (usually about 120–140° C. under reduced pressure) has been reached. It should be noted that the desired compound is found in the sublimation residue and not in the sublimate, as most often found in sublimation purifications.

Depending upon several factors, such as how much of the primary impurities, e.g., the corresponding dipyrromethane, other oligomers and polymers, have already been removed from the residue and the volatility of the dipyrromethane, the use of sublimation in step (c) fairly quickly produces a composition of more than 5%, i.e., from 5–100%, of the desired tripyrrane, which also contains less than 95%, i.e., 0 to 95%, of the corresponding dipyrromethane contaminant. However, preferably, the composition contains more than 50%, i.e., from about 50–100%, more preferably 95–100%, of the desired tripyrrane and less than 50%, more preferably less than about 5%, of the corresponding dipyrromethane.

When sublimation is used in step (c), it preferably takes place under reduced pressure, more preferably from about 10 to about 0.01 mm Hg and, most preferably, at about 0.1 mm Hg. The sublimation temperature should be sufficiently high to ensure an acceptable rate of sublimation, without being so high as to cause decomposition of the product or sublimation of the desired tripyrrane. The sublimation temperature will also be affected by the pressure under which the sublimation is being carried out, with the temperature necessary for sublimation generally decreasing as the pressure is reduced. At about 1 mm Hg, the temperature typically varies from about 120 to 140° C. and, preferably, is maintained at about 130° C. Particularly when using the sublimation method of purification, the tripyrrane can be prepared in solid form on a large scale, can be fully characterized, and has excellent purity.

Generally, for example, a meso-disubstituted tripyrrane can be synthesized by stirring together the appropriately substituted aldehyde and the appropriate pyrrole in a molar ratio of about 1:20 with a catalytic amount of trifluoroacetic acid ("TFA") at room temperature under nitrogen for about 10–20 minutes. The excess pyrrole is evaporated off under vacuum, usually resulting in an oil.

In a preferred embodiment, the product is isolated to some extent, such as by dissolving in an eluting solvent and chromatographed through a short column of silica gel to remove polymeric material. If present, the eluting solvent is then evaporated off, and the residue is heated to sublime off the unwanted dipyrromethane, leaving the desired meso-disubstituted tripyrrane at about a 95% purity level. This method is particularly favored when the tripyrrane is being made from a β-unsubstituted pyrrole (where both R groups are hydrogens) and is based on the method described by Lee et al., *Tetrahedron*, 50:39, 11427–40 (1994).

Alternatively, a meso-disubstituted tripyrrane can be made by refluxing together the appropriately substituted aldehyde and an excess amount of the appropriate pyrrole in an organic solvent with a catalytic amount of p-toluenesulfonic acid. This method is based on a procedure mentioned in the notes and references section of Rebek et al., *Tetrahedron Letters*, 35:37, 6823 (1994), which refer to T. Carell, Ph.D. thesis, Ruprechts-Karl-Universitat Heidelberg (1994). The reaction mixture is filtered through silica, and the solvent is evaporated off. The residue is then heated to separate the two main products: the dipyrromethane and the meso-disubstituted tripyrrane. As described above, it is the undesired dipyrromethane that sublimes off, leaving the desired tripyrrane behind.

This second method is particularly suitable for preparing tripyrranes that are made from a β-substituted pyrrole since, in these cases, the pyrrole is not generally relied upon as the sole solvent. Using either the first or second method, however, about a 10% yield of a tripyrrane product that demonstrates excellent purity is achieved and by a process that is amenable to large-scale synthesis of multi-gram quantities.

The meso-disubstituted tripyrrane compounds of Formula I may be easily converted to the corresponding dialdehyde under standard Vilsmeier-Haak conditions, as shown below:

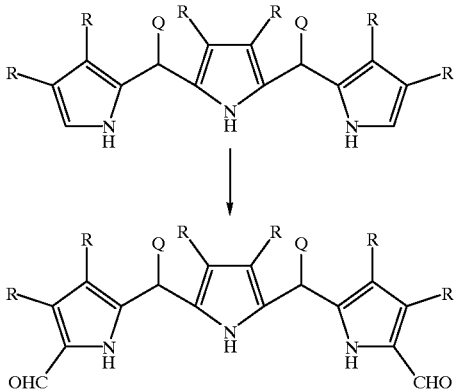

By "standard Vilsmeier-Haak conditions" is meant the use of a either excess dimethylformamide (DMF)/phosphoryl chloride ($POCl_3$) or DMF/benzoyl chloride, at 80° C. for 1–6 hours, followed by hydrolysis in aqueous sodium acetate and, if necessary, chromatography, in accordance with A. Haussner et al., *Organic Syntheses Based on Name Reactions and Unnamed Reactions*, Pergamon, Oxford, 1st reprint, 399 (1995), the disclosure of which is hereby incorporated by reference.

The meso-substituted tripyrrane compounds of the invention may be reacted with a wide variety of appropriately functionalized heterocyclic and carbocyclic rings to produce a large number of possible 5,10-disubstituted porphyrins, expanded porphyrins, and miscellaneous other polypyrrolic macrocycles, all of which would be difficult to make by any other known method. For example, a compound of Formula I can be cyclized with a compound of Formula II, or two moles of a compound of Formula I can be condensed with two moles of Q—CHO, seen above.

Figure 2:
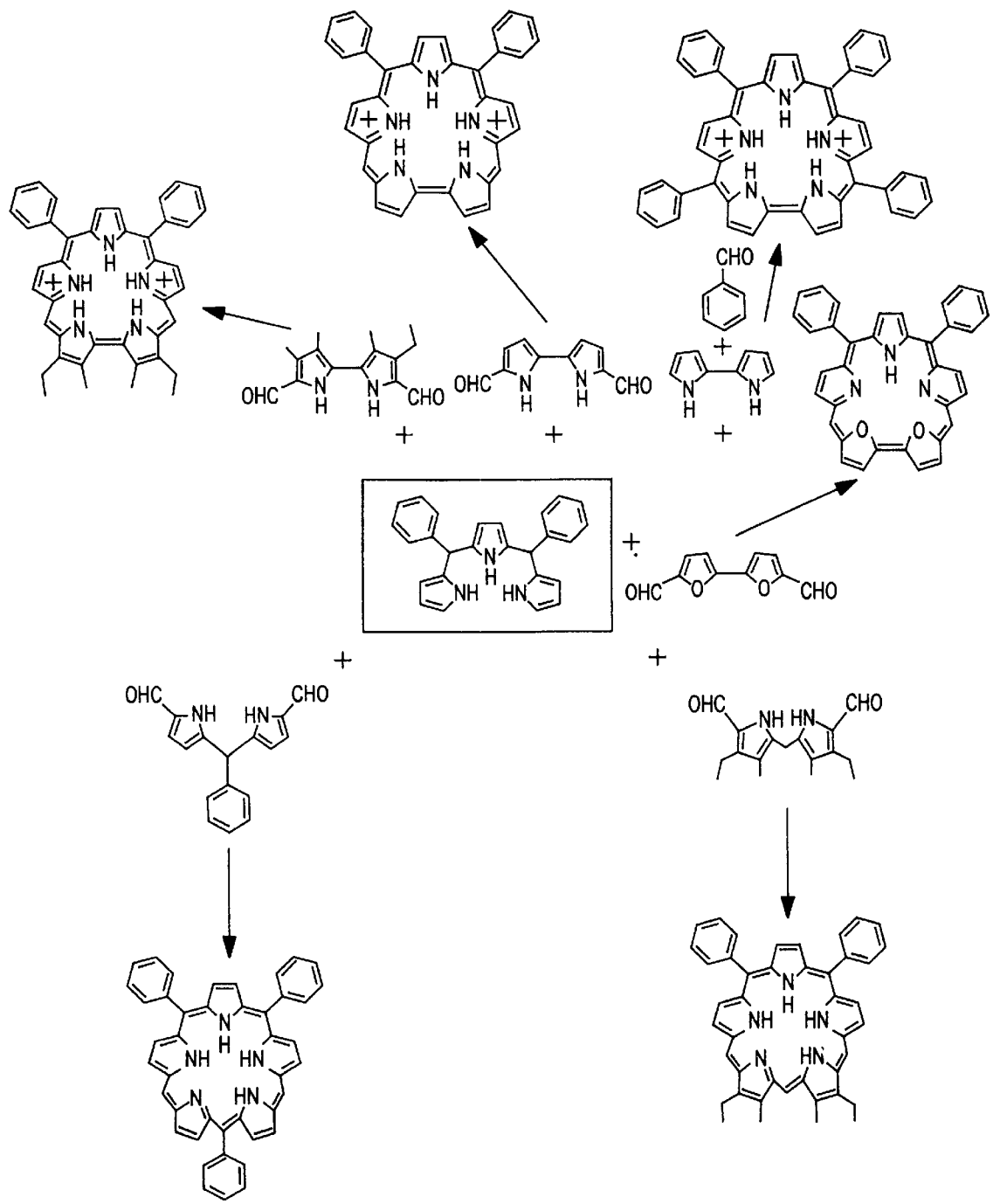
FIG. 2 shows the formation of a number of pentapyrrolic compounds.

Specific examples of reactions of the compound of Formula I with a considerable number of different monopyrrolic heterocyclic reactants to form an array of polypyrrolic products are illustrated in FIG. 1. The meso-disubstituted tripyrrane compounds of the invention may also be reacted with appropriately functionalized 5-membered, bi-heterocyclic compounds to produce a wide variety of possible 5,10-disubstituted sapphyrins and pentaphyrins. Specific examples of possible reactions with these bicyclic reactants to produce macrocyclic products are illustrated in FIG. 2.

Figure 3:
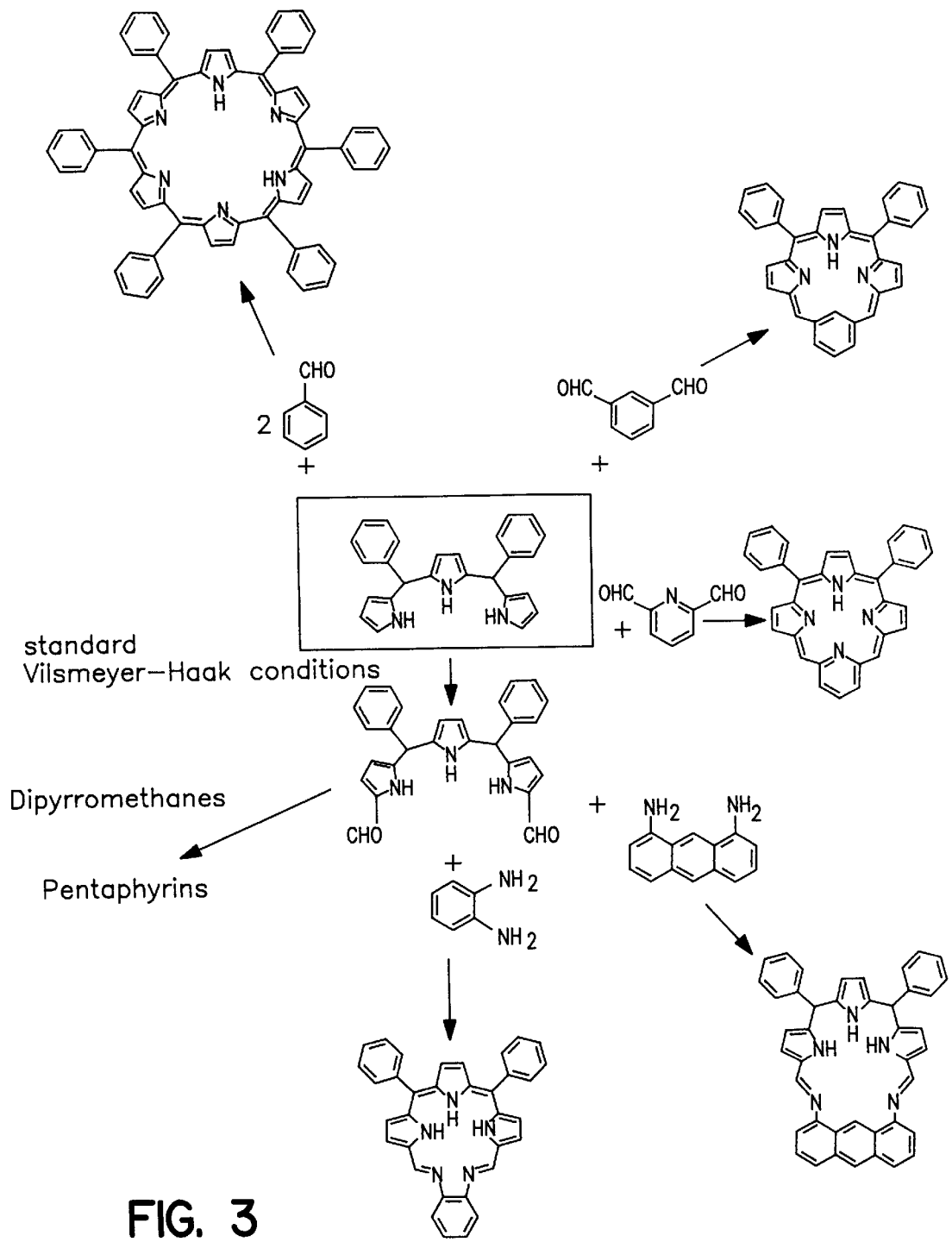
FIG. 3 shows the formation of a number of miscellaneous polypyrrolic macrocyclic compounds.

Still other miscellaneous mono- or bicyclic, hetero- or carbocyclic compounds can be reacted with the meso-substituted tripyrrane compounds to produce a great variety of pentaphyrins, hexaphyrins and texaphyrins. Specific examples of these reactants and products are illustrated in FIG. 3. Thus, the meso-disubstituted tripyrrane of Formula I may be used as a key intermediate to make a large library of other polypyrrolic compounds, most of which are useful in the areas described above.

Generally speaking, the preparation of 5,10-disubstituted porphyrins and other 5,10-disubstituted polypyrrolic macrocycles includes two basic steps:

(a) an acid-catalyzed cyclization step; and (b) an oxidation step, typically, to form a fully conjugated macrocycle, which can often be performed in situ.

Typically, an additional step (c) is also used to isolate the product to some extent.

In one embodiment, the cyclization step (a) involves the reaction of the tripyrrane compound of Formula I having two terminal pyrrole rings, each having an unsubstituted α-position, with a planar cyclic co-reactant having a formula selected from the group consisting of:

Q—CHO, Q—CH(OS)(OS'),

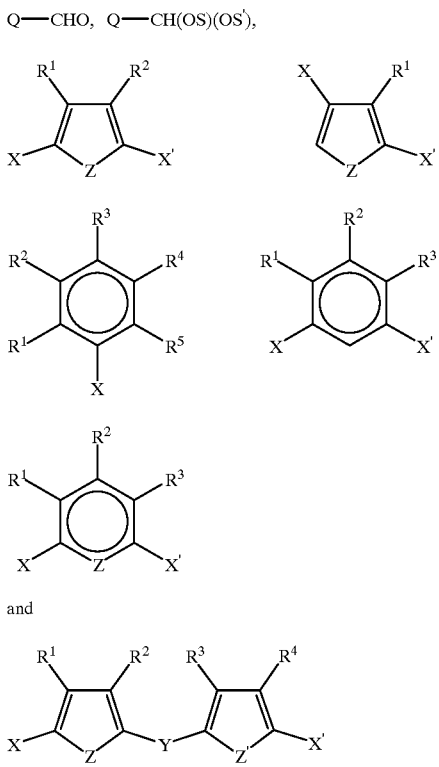

and where S and S' are as defined above, and Z and Z' are independently —N—, >NH, —O— or a bivalent sulfur atom, preferably —N— or >NH.

$R^1$–$R^5$ are independently hydrogen, lower alkyl, alcohol or carbonyl-containing groups. Preferably, $R^1$–$R^5$ are selected from the group consisting of hydrogen, methyl, ethyl, n-propyl, i-propyl, n-butyl, tert-butyl, —$C_8H_{17}$, —$OCH_3$, —$O(CH_2CH_2O)_3CH_2CH_3$, —$CH_2OH$, —$(CH_2)_4$ OH, —$O(CH_2)_3OH$, —$(CH_2)_2COOH$, —$(CH_2)_2COOCH_3$, and —$(CH_2)_2COOC_2H_5$.

X and X' in the above formulas are groups capable of coupling with the unsubstituted α-positions of the terminal pyrrole rings of the compound of Formula I. Preferably, X and X' have the formula —CHO or —CHR'—L where R' is hydrogen, alkyl such as methyl or ethyl, or aryl such as phenyl, pyridyl, or phenanthrenyl; and L is a good leaving group. By "leaving group" is meant a moiety, such as —$NH_2$, —OH or —OAc, that is readily lost under acid catalysis to form a cationic intermediate, i.e., a "—$CH_2^+$" group. This cationic intermediate then attacks in a nucleophilic fashion the α-position of the tripyrrane. In a particularly preferred embodiment, X and X' are selected from the group consisting of —CHO, —$CH_2OH$, —$CH_2NH_2$, and —CH(Ar)—OH where Ar is aryl having from 5 to 7 ring carbons.

Y in the above formula can be a direct link, alkylene, pyrrolylene, furanylene, phenylene, thiophenylene, benzylene, or alkylene-pyrrolene-alkylene. However, preferably, Y is selected from the group consisting of a direct link, —$CH_2$—, pyrrolene, furanylene, thiophenylene, benzylene and —$CH_2$-pyrrolene-$CH_2$—.

In the cyclization step (a), the molar ratio of the tripyrrane of Formula I to the planar co-reactant can vary greatly between the ranges of about 10:1 to about 1:50, preferably from about 1:1 to about 1:2, depending upon the reactivity of the reactants.

Typically, a suitably non-reactive organic solvent is used to dissolve at least one of the starting materials, thus facilitating the cyclization reaction. When a solvent is used, it can be any one of a wide variety of organic solvents capable of dissolving at least one of the reactants and, yet, does not interfere with the course of the reaction to any significant degree. Preferably, such a solvent should also have a boiling point sufficiently low to evaporate off quickly during the process of isolating and/or purifying the product.

Examples of suitable solvents include alcohols, such as methanol, ethanol, i-propanol, n-butanol, 2-ethylhexanol, benzyl alcohol, glycerol, and dimethoxyethane; ethers such as diethyl ether and n-butyl ether; aromatic solvents, such as benzene, toluene, and aniline; ketones such as acetone and methyl ethyl ketone; esters such as ethyl acetate, butyl acetate, and ethyl benzoate; and chlorinated solvents such as carbon tetrachloride, chloroform, dichloromethane, and 1,1,1-trichloroethane.

A cyclization agent can be used in step (a) and, typically, is a Lewis or Bronsted acid. Examples of suitable cyclization agents include mineral acids such as hydrobromic acid (HBr), hydrochloric acid (HCl) and sulfuric acid ($H_2SO_4$); other acids such as boron trifluoride etherate ($BF_3Et_2O$), acetic acid, trichloroacetic acid ($CCl_3COOH$), trifluoroacetic acid ($CF_3COOH$), and triflic acid ($CF_3SO_3H$); sulfonic acids such as benezenesulfonic acid, p-toluenesulfonic acid and trifluoromethane sulfonic acid; metal halides such as $SnCl_4$, $AlCl_3$, $FeCl_3$, and fused zinc chloride; solid-phase, bound acids, such as cation exchange resins and other polymeric acids or clays, such as montmorillonite; and mixtures of such cyclization reagents. In a particularly preferred embodiment, the cyclization agent is p-toluenesulfonic acid, the etherate $BF_3Et_2O$ or trifluoroacetic acid.

The cyclization agent can be present in widely varying amounts from catalytic amounts up to 0.01 to 10 times the molar amount of tripyrrane present. Preferably, the acid is present in a molar concentration ranging from catalytic to about 5 times the molar amount of the tripyrrane.

Examples of particularly suitable combinations of cyclization agent and non-reactive solvent include p-toluenesulfonic acid in ethanol; the etherate $BF_3Et_2O$ or trifluoroacetic acid in dichloromethane; and p-toluenesulfonic acid in toluene.

The cyclization reaction temperature in step (a) can vary widely depending on the solubility of the reactants in the solvent being used, the reactivity of the reactants and the thermal stability of the reactants. The temperature should not be so high as to decompose the reactants or so low as to inhibit the reaction or freeze the solution. In most cases, the reaction in step (a) can take place conveniently at room temperature, and room temperature is preferred for reasons of convenience. However, occasionally, some heat is advantageous, primarily to facilitate the dissolution of the starting materials being used in the organic solvent employed.

The cyclization reaction can be carried out at pressures both above and below atmospheric pressure. Preferably, however, the reaction is carried out at a pressure about equal to atmospheric pressure. The reaction can be carried out in the presence of a mixture of gases approximating air but, when particularly reactive reactants are involved, the gaseous mixture may be enriched with an inert gas, such as nitrogen gas, argon and the like.

The time required for the cyclization reaction of the tripyrrane of Formula I and the above-described planar co-reactant will depend to a large extent on the temperature used and the relative reactivities of the starting materials. Particularly when the meso-substituents of the tripyrrane compound are aryl, heteroaryl, or a bulky alkyl group such as tert-butyl, the time required for the reaction to take place may increase due to steric hindrance. Therefore, the reaction time can vary greatly, for example, from about 30 minutes to about 24 hours. Preferably, the time required for the cyclization of the tripyrrane of Formula I with the planar co-reactant is in the range of about 30 to 60 minutes, unless the cyclization step (a) is combined with the oxidation step (b), either sequentially or simultaneously. When (a) and (b) are combined or occur simultaneously, the reaction time will be controlled by the time needed for the completion of both reactions and, typically, will be somewhat longer, for example, from about 8 to 25 hours, most preferably about 12 hours.

Optionally, various techniques such as different types of chromatography, especially thin layer chromatography (TLC) or gas chromatography (GC), and optical spectroscopy, can be used to follow the progress of the reaction by the disappearance of the starting materials.

At the conclusion of the cyclization reaction, a reaction mixture results, which is typically used directly in the oxidation step (b) without the intervening isolation or purification of the intermediate(s) present in the reaction mixture.

The oxidation of the cyclization reaction mixture to form the desired 5,10-disubstituted porphyrin or other 5,10-disubstituted tetrapyrrolic macrocyclic compound can be accomplished by any of the usual oxidizing agents generally suitable to accomplish this type of aromatization. Examples of such useful oxidizing agents include dichlorodicyanobenzoquinone ("DDQ"), o- and p-chloranil, $O_2$ gas, iodine ($I_2$) and the like. Most of the above oxidizing agents are used in combination with the non-reactive organic solvent used during the cyclization step. Particularly preferred combinations of oxidizing agents and solvents for step (b) are selected from the group consisting of DDQ or p-chloranil in dichloromethane or toluene, or $O_2$ gas bubbled through an alcohol solvent such as methanol or ethanol.

The rate of the reaction is often influenced by the type and combination of oxidizing agent and solvent, whether it takes place as a separate sequential step or occurs simultaneously with the cyclization step. Simultaneous cyclization and oxidation can take place with, for example, the simultaneous use of an alcohol solvent such as methanol or ethanol, an aromatic acid reactant such as p-toluenesulfonic acid, and oxygen gas bubbling through the reaction mixture. Other examples include the combination of a solvent such as chloroform with air being used as the oxidizing agent.

The temperature of the reaction mixture during the oxidation step (b) can vary widely depending upon the oxidizing agent being used. For example, when DDQ in toluene is being used, reflux temperature is generally appropriate. On the other hand, when oxygen gas is being used as the oxidizing agent with an ethanol solvent, ambient temperature is a suitable temperature. When other oxidizing agents are used, the temperature is typically maintained in the range of about 1 to 100° C. and, preferably, is allowed to remain at about room temperature or at the reflux temperature of the reaction mixture.

The time required for the oxidation reaction of step (b) will depend to a large extent on the temperature used and the relative reactivities of the starting materials being used. However, the time typically varies from about 15 minutes to about 24 hours, usually from about 20 minutes to an hour for room temperature reactions. If the oxidation takes place simultaneously with the cyclization reaction, as described above, the time required for both reactions can be as long as two days but, usually, is about 10 to 15 hours.

The oxidation reaction of step (b) can be carried out in the presence of gases at a pressure both above and below atmospheric pressure. Most frequently, however, the reaction is carried out at a pressure about equal to atmospheric pressure.

The resulting product, a 5,10-disubstituted porphyrin or other 5,10-disubstituted polypyrrolic macrocyclic compound, can be isolated by any conventional method, such as by drowning out in a non-solvent, precipitating out, extraction with any immiscible liquid, evaporation of a solvent, or some combination of these or other conventional methods. Typically, after being isolated, the product is then purified by any one, or a combination, of known purification techniques, such as recrystallization, various forms of chromatography, trituration with a non-solvent or a partial solvent, vacuum distillation, countercurrent extraction techniques, and the like.

It is preferable to isolate and/or purify the 5,10-disubstituted porphyrin or other 5,10-disubstituted polypyrrolic macrocycle by the use of chromatography. For example, the resulting oil or solid product obtained after the oxidation step (b) (usually by evaporation of any solvent used in the cyclization and/or oxidation) is dissolved in an eluting solvent and chromatographed through a column of silica gel or alumina to remove impurities. The appropriate fractions are collected, and the eluting solvent is then evaporated off, leaving the product as the residue.

In an alternative embodiment, an α,α'-dialdehyde tripyrrane of Formula II is cyclized in step (a), in the presence of an acid catalyst, with either (i) a planar cyclic co-reactant having a formula selected from the group consisting of:

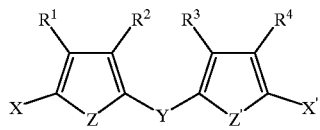

and

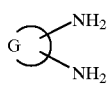

wherein:

$R^1$–$R^4$, Z and Z', and Y are as described above;

X and X' are independently hydrogen or —COOH; and

G represents the atoms necessary to complete a carbocyclic or heterocyclic ring having from 5 to 14 ring atoms, or (ii) a compound of Formula I, to form a cyclized intermediate, which is then oxidized to form the corresponding 5,10-disubstituted porphyrin compound or other 5,10-disubstituted polypyrrolic macrocycle. The dialdehyde tripyrrane of Formula II can be prepared from the α,α'-unsubstituted tripyrrane of Formula I under standard Vilsmeier-Haak conditions, as described above.

In the cyclization step (a), the molar ratio of the tripyrrane of Formula II to the planar co-reactant can vary greatly, depending upon the reactivity of the reactants.

Typically, a suitably non-reactive organic solvent is used to dissolve at least one of the starting materials, thus facilitating the cyclization reaction. When a solvent is used, it can be any one of a wide variety of organic solvents capable of dissolving at least one of the reactants and, yet, does not interfere with the course of the reaction to any significant degree. Preferably, such a solvent should also have a boiling point sufficiently low to evaporate off quickly during the process of isolating and/or purifying the product.

Examples of suitable solvents include alcohols, such as methanol, ethanol, i-propanol, n-butanol, 2-ethylhexanol, benzyl alcohol, glycerol, and dimethoxyethane; ethers such as diethyl ether and n-butyl ether; aromatic solvents, such as benzene, toluene, and aniline; ketones such as acetone and methyl ethyl ketone; esters such as ethyl acetate, butyl acetate, and ethyl benzoate; chlorinated solvents such as carbon tetrachloride, chloroform, dichloromethane, and 1,1,1-trichloroethane; and the like.

A cyclization agent can be used in step (a) and, typically, is a Lewis or Bronsted acid. Examples of suitable cyclization agents include mineral acids such as hydrobromic acid (HBr), hydrochloric acid (HCl) and sulfuric acid ($H_2SO_4$); other acids such as boron trifluoride etherate ($BF_3Et_2O$), acetic acid, trichloroacetic acid ($CCl_3COOH$), trifluoroacetic acid ($CF_3COOH$), and triflic acid ($CF_3SO_3H$); sulfonic acids such as benezenesulfonic acid, p-toluenesulfonic acid and trifluoromethane sulfonic acid; metal halides such as $SnCl_4$, $AlCl_3$, $FeCl_3$, and fused zinc chloride; solid-phase, bound acids, for example, cation exchange resins, and other polymeric acids and clays, such as montmorillonite clay, and mixtures of such cyclization reagents. In a particularly preferred embodiment, the cyclization agent is p-toluenesulfonic acid, the etherate $BF_3Et_2O$, or trifluoroacetic acid.

The cyclization agent can be present in widely varying amounts from catalytic amounts up to several times the molar amount of tripyrrane present.

Examples of particularly suitable combinations of cyclization agent and non-reactive solvent include p-toluenesulfonic acid in ethanol; the etherate $BF_3Et_2O$ or trifluoroacetic acid in dichloromethane; p-toluenesulfonic acid in toluene; and the like.

The cyclization reaction temperature in step (a) can vary widely depending on the solubility of the reactants in the solvent being used, the reactivity of the reactants, and the thermal stability of the reactants. The temperature should not be so high as to decompose the reactants or so low as to inhibit the reaction or to freeze the solution. In most cases, the reaction in step (a) can take place conveniently at room temperature, and room temperature is preferred for reasons of convenience. However, occasionally, some heat is advantageous, primarily to facilitate the dissolution of the starting materials being used in the organic solvent employed.

The cyclization reaction can be carried out at pressures both above and below atmospheric pressure. Preferably, however, the reaction is carried out at a pressure about equal to atmospheric pressure. The reaction can be carried out in the presence of a mixture of gases approximating air but, when particularly reactive reactants are involved, the gaseous mixture may be enriched with an inert gas, such as nitrogen gas, argon and the like.

The time required for the cyclization reaction of the tripyrrane of Formula I and the above-described planar co-reactant will depend to a large extent on the temperature used and the relative reactivities of the starting materials. Particularly when the meso-substituents of the tripyrrane compound are aryl, heteroaryl, or a bulky alkyl group such as tert-butyl, the time required for the reaction to take place may increase due to steric hindrance. Therefore, the reaction time can vary greatly, for example, from a few minutes to several hours. When steps (a) and (b) are combined or occur simultaneously, the reaction time will be controlled by the time needed for the completion of both reactions and, typically, will be somewhat longer, for example, from several hours to several days.

Optionally, various techniques such as different types of chromatography, especially thin layer chromatography (TLC), gas chromatography (GC) or optical spectroscopy, can be used to follow the progress of the reaction by the disappearance of the starting materials. The macrocycles initially formed will, if applicable, be readily oxidized to the corresponding aromatic compound. The isolation and purification procedures for this embodiment are equivalent to those described for the resulting macrocycle above.

Examples of macrocycles that can be made by one of the above methods include:
3,22-diethyl-2,23-dimethyl-10,15-diphenylsapphyrin;
5,10-diphenylsapphyrin;
5,10,15,20-tetraphenylsapphyrin;
5,10,15,20,25,30-hexaphenylhexaphyrin;
17,23-diethyl-18,22-dimethyl-5,10-diphenylpentaphyrin; and
18,22-dithyl-17,22-dimethyl-5,10-diphenyl pentaphyrin.

The invention will be further clarified by the following examples, which are intended to be purely illustrative of the invention.

EXAMPLE 1

Preparation of 5,10-Diphenyltripyrrane(4)

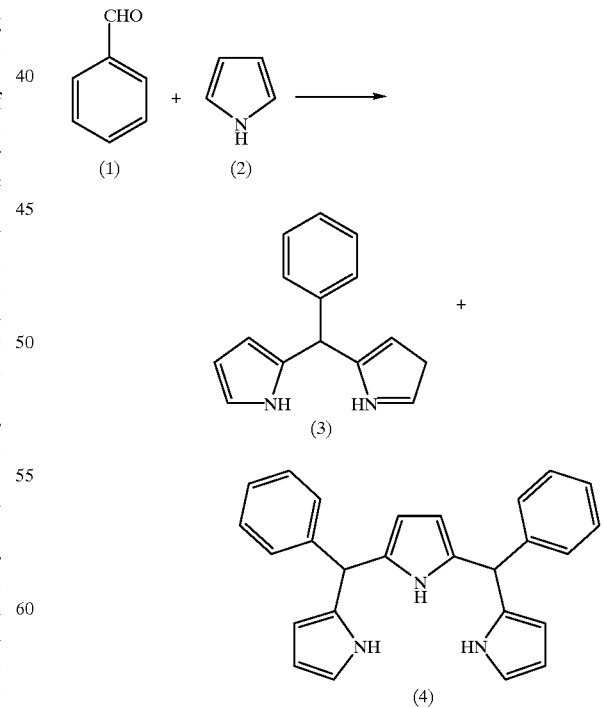

Method A: (Particularly applicable to an unsubstituted pyrrole starting material):

6.0 ml of benzaldehyde (1) (59 mmol) was mixed with 150 ml of pyrrole (2) (2.16 mol), and the resulting mixture was deoxygenated by bubbling dry $N_2$ through it for 15 minutes. While still under nitrogen, 0.45 ml of trifluoroacetic acid (5.8 mmol) was added, and the reaction mixture was stirred for 15 minutes at room temperature (about 20° C.). After this, the reaction mixture was evaporated under vacuum (5 torr) with slight heating on a rotary evaporator to yield a dark oil. The oil was taken up in a minimal amount of methylene chloride and charged onto a flash chromatography column (silica gel, 5.5×30 cm., methylene chloride). The colorless fractions containing the dipyrromethane (3), the tripyrrane (4), and some small amounts ($\leq 1\%$) of an unidentified material were collected. Thin layer chromatography ("TLC") was used to follow the process in this manner: The TLC plates used were commercially available Merck silica TLC aluminum sheets (silica gel 60 $F_{254}$). Upon treatment with fuming $Br_2$, the TLC spot corresponding to the dipyrromethane (3) turned bright orange, and the spot corresponding to the desired tripyrrane (4) turned beige. The collected fractions were placed on a rotary evaporator to evaporate off the solvent, yielding a tan oil.

It was found that the dipyrromethane (3) and tripyrrane (4) could be separated in very small batches (100 mg) of the tan oil by the use of prepared TLC plates made with a 1.0 mm silica coating and using $CH_2Cl_2/CCl_4$ (1:1) as the eluting solvent. Specifically, the TLC plates used were pre-coated Whatman or Merck silica gel plates (available with or without fluorescence indicator), 20×20 cm; 0.5, 1.0 or 2.5 mm thickness. The $R_f$ value for the desired tripyrrane (4) was 0.63; the $R_f$ value for the dipyrromethane (3) was 0.78. However, this chromatographic method would not be useful for preparing even multiple-gram quantities, let alone industrial scale quantities.

The remainder of the tan oil was transferred into a sublimation apparatus and subjected to a high vacuum (0.1 torr). A slow heating rate (about 0.75° C./minute) was maintained until visible sublimation began at 130° C. After all sublimation ceased, a white crystalline sublimate, consisting of 7.20 g of the dipyrromethane (3) (54.6% yield), was collected, leaving 2.45 g (11% yield) of an orange, glassy sublimation residue, which consisted mainly of the desired tripyrrane 4. The level of purity was $\geq 95\%$, based on an $^1$H-NMR spectrum of the residue in $CDCl_3$, as shown in FIG. 4.

Method B: (Particularly applicable to β-substituted pyrrole starting materials):

12.0 ml of benzaldehyde (1) (0.118 mol) was dissolved in 750 ml of toluene with 52 ml of pyrrole (2) (0.745 mol). A catalytic amount (100 mg) of p-toluenesulfonic acid monohydrate ($4.9 \times 10^{-4}$ mol) was added to the solution, and the reaction mixture was refluxed under $N_2$ for one hour. After this, the reaction mixture was evaporated on a rotary evaporator to give a dark oil. The oil was subjected to much the same chromatography/sublimation treatment as described above for Method A. Specifically, the reaction mixture was filtered through silica, and the solvent was evaporated off. The residue was then heated to separate the two products: the phenyl dipyrromethane and the meso-diphenyltripyrrane. The dipyrromethane sublimed off, leaving the tripyrrane behind as a light tan glass material. This gave a 44% yield of the dipyrromethane (3) and 9.8% of the desired tripyrrane at the same purity levels produced above in Method A (about 98%).

Analytical Data for Tripyrrane:
mp: 75–80° C.;
$^1H^{NMR}$ (200 MHz, $CD_2Cl_2$): 5.35 (s, 2H), 5.78 (d, J=4 Hz, 2H), 5.89 (s, 2H), 6.14 (dd, second order, J=4.4 Hz, 2H), 6.66 (dd, second order, J=4.4 Hz, 2H), 7.15–7.38 (m, 10H), 7.75 (br s, 1H), 7.88 (br s, 2H)

$^{13}$H-NMR (50 MHz, $CDCl_3$): 44.1, 107.2, 107.4, 108.4, 117.2, 127.0, 128.4, 128.6, 132.3, 132.5, 142.1

HR-MS (EI, 200° C. : Expected for $^{12}C_{26}H_{23}N_3$: 377.1892; found 377.1881.

| Elemental Analysis for $C_{26}H_{23}N_3$ (377.49 g/mol) | | | |
|---|---|---|---|
| Element: | C | H | N |
| Calculated: | 82.73 | 6.14 | 11.13 |
| Found: | 82.16 | 6.03 | 10.72 |

EXAMPLE 2

Preparation of 3,22-Diethyl-2,23-dimethyl-10-15-diphenylsapphyrin (6)

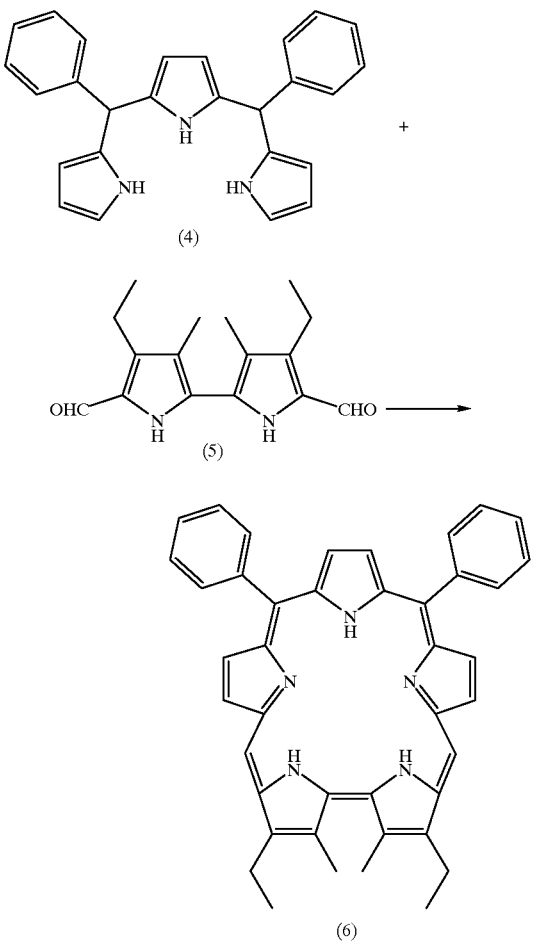

22.6 mg of the tripyrrane (4) ($6.0 \times 10^{-5}$ mol) and 16.3 mg of bipyrrolebis(aldehyde) (5) ($6.0 \times 10^{-5}$ mol) were dissolved in 60 ml of absolute ethanol, and $O_2$ was bubbled through the solution. 45.6 mg of p-toluenesulfonic acid monohydrate ($2.4 \times 10^{-4}$ mol) was added, and $O_2$ bubbling was continued for 12 hours. The solution was then evaporated on a rotary evaporator to dryness. The resulting solid was chromatographed on alumina (neutral, activity I, 2×12 cm) with 2.5% $MeOH/CH_2Cl_2$. The yellow-green main fraction was collected, and the solvent was evaporated off to give 14.3 mg of the product (6) as the free base (39% yield). The free base was quantitatively converted into its corresponding dark green bis-hydrochloride by shaking a $CHCl_3$ solution of product (6) with a 20% aqueous HCl solution, followed by the addition and separation of an organic phase, drying over anhydrous $Na_2SO_4$, and evaporating to dryness.

Analytical Data:

mp: $\geq 250°$ C.;

HR-MS (EI, 210° C.): Calculated for $^{12}C_{42}H_{39}N_5$: 613.32056; found: 613.31842

$^1$H-NMR (200 MHz, $CDCl_3$) of the dihydrochloride: −4.48 (s, 2H), −4.36 (s, 2H), −3.87 (s, 1H), 2.20 (tr, J=5.2 Hz, 6H), 4.18 (s, 6H), 4.58 (q, J=5.2 Hz, 4H), 7.90–8.05 (m, 6H), 8.61 (d, J=4.4 Hz, 4H), 9.28 (d, J=0.8 Hz, 2H), 9.57 (dd, J=3.2, 0.8 Hz, 2H), 10.20 (dd, J=3.2, 0.8 Hz, 2H), 11.78 (s, 2H)

UV-Vis [$CH_2Cl_2$, trace of $Et_3N$] $\lambda_{max}$ (rel. intensity): 458(1.0), 626(0.43), 652(0.45), 684(0.54), 718(0.49), 802 (0.14)

UV-Vis [$CH_2Cl_2$, trace of TFA] $\lambda_{max}$ (rel. intensity): 486(1.0), 772(0.28)

EXAMPLE 3

Preparation of 5,10-diphenylsapphyrin (8)

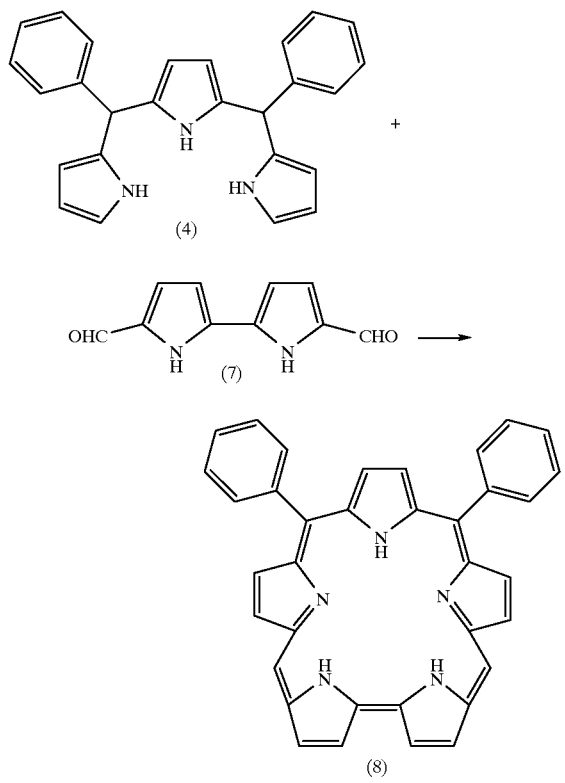

188 mg of the tripyrrane (4) (4.99×10$^{-4}$ mol) and 94 mg of bipyrrolebis(aldehyde) (7) (5.0×10$^{-4}$ mol) were dissolved with the use of a heat gun in 450 ml of absolute ethanol, and $O_2$ was bubbled through the solution. 95 mg of p-toluenesulfonic acid monohydrate (2.0×10$^{-3}$ mol) dissolved in 3 ml of ethanol were added, and the reaction mixture was bubbled with $O_2$ for an additional 12 hours. After this, the reaction mixture was evaporated on a rotary evaporator to dryness. The resulting black residue was triturated with $CHCl_3$. The combined dark green extracts were evaporated to dryness and chromatographed on a prepared TLC plate (0.5 mm alumina) with 0.1% $Et_3N$/$CH_2Cl_2$. The green-yellow band was collected and eluted with 0.5% MeOH/$CH_2Cl_2$. The solvent was evaporated off to give 14.8 mg of the product (8) (5.5% yield). The product (8) was converted quantitatively into its corresponding dihydro-p-toluenesulfate by adding a slight excess of p-toluenesulfonic acid to a $CHCl_3$ solution of product (8), followed by precipitation of the salt by slow diffusion of hexane into this solution.

Analytical Data:

$^1$H-NMR (400 MHz, $CDCl_3$) of the bis(p-toluenesulfate) salt: −4.68 (s, 2H), −4.46 (s, 2H), −3.85 (s, 1H), 2.45 (s, 6H), 7.26 (d, J=8 Hz, 4H), 7.79 (d, J=8 Hz, 4H), 7.95–8.05 (m, 6H), 8.66 (d, J=7 Hz, 4H), 9.32 (d, J=0.8 Hz, 2H), 9.64 (dd, J=3.9, 0.9 Hz, 2H), 10.25 (dd, J=4.7, 0.9 Hz, 2H), 10.47 (dd, J=4.7, 0.7 Hz, 2H), 10.78 (dd, J=4.4, 0.8 Hz, 2H), 11.92 (s, 2H)

HR-MS (EI, 180° C.):

Calculated for $^{12}C_{36}H_{25}N_5$: 527.21100; found: 527.21015

UV-Vis [$CH_2Cl_2$, trace of $Et_3N$] $\lambda_{max}$ (rel. intensity): 384, 478(1.0), 506(0.69), 626, 686, 708, 786

UV-Vis [$CH_2Cl_2$, trace of TFA] $\lambda_{max}$ (rel. intensity): 494(1.0), 656, 682, 724(sh), 758(0.21)

EXAMPLE 4

Preparation of 5,10,15,20-tetraphenylsapphyrin (10)

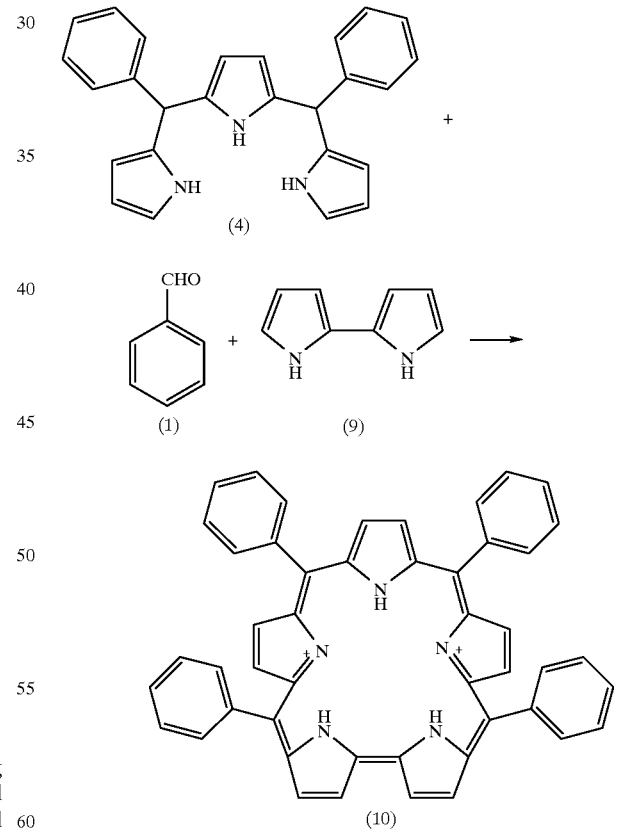

75 mg of the tripyrrane (4) (2.00×10$^{-4}$ mol), 42.4 mg of benzaldehyde (7) (4.0×10$^{-4}$ mol), and 26.4 mg of the bipyrrole (9) (2.0×10$^{-4}$), were dissolved in 20 ml of $CH_2Cl_2$, and $N_2$ was bubbled through the solution for 15 minutes. One drop of $BF_3Et_2O$ was added, and the solution was stirred for one hour under $N_2$. Following this, 100 mg of p-chloranil ($4.0 \times 10^{-4}$) was added, and the reaction mixture was refluxed for 20 minutes. The solution was charged onto a plug of alumina (basic, activity I, 2×5 cm) and filtered. The filtrate was evaporated to dryness, and the resulting solid was chromatographed on a prepared TLC plate (0.5 mm alumina) with 1:1 $CCl_4/CH_2Cl_2$. The green band was collected and eluted with $CH_2Cl_2$. The solvent was evaporated off to give 7.4 mg of the product (10) as a bright green microcrystalline material (5.5% yield). By UV-Vis, MS, and NMR of the protonated and non-protonated forms, the material was proved to be identical to 5,10,15,20-tetraphenylsapphyrin, as described by Chmielewski et al., *Eur. J. Chem.*, 1:1, 68–73 (1995).

Analytical Data:

HR-MS (EI, 250° C.) Calculated for $^{12}C_{48}H_{33}N_5$: 679.27362; found: 679.27357

UV-Vis [$CH_2Cl_2$, trace of $Et_3N$] $\lambda_{max}$ (log epsilon): 492 (4.01), 518(3.80), 638(3.90), 698(3.16), 718(sh), 798(3.88)

UV-Vis [$CH_2Cl_2$, trace of TFA] $\lambda_{max}$ (rel. intensity): 488(1.0), 410(sh), 672(0.06), 736(0.11), 790(0.18)

EXAMPLE 5

Preparation of 5,10,15,20,25,30-hexaphenylhexaphyrin (11)

$CH_2Cl_2$. After the solution was purged with $N_2$ for 10 minutes, 15 μl of trifluoroacetic acid was injected, and the mixture was stirred for 50 minutes. 91 mg of dichlorodicyano-p-quinone ($4.0 \times 10^{-4}$ mol) was added, and the mixture was stirred for an additional hour. The solvent was removed by evaporating on a rotary evaporator, and the resulting solid was repeatedly chromatographed on prepared TLC plates (0.5 mm silica). The eluting solvent was 20% EtOAc in $CH_2Cl_2$ with a few drops of $Et_3N$ added. The blue band, consisting of the product (11), was isolated and eluted.

Analytical Data:

HR-MS (EI, 350° C.):

Calculated for $^{12}C_{66}H_{44}N_6$: 920.36273; found: 920.36550

UV-Vis [$CH_2Cl_2$] $\lambda_{max}$ (rel. intensity): 385(0.95), 466 (0.46), 520(0.50), 636(1.0)

The $^1$H-NMR spectrum was complex, which may reflect a non-static confirmation. This has also been observed for β-alkyl hexaphyrins (see Charriere et al., *Heterocycles*, 36:7, 1561 (1993)) and the sapphyrin (10) (see Chmielewski et al., *Eur. J. Chem.*, 1:1, 68–73 (1995)). Because the compound (11) incorporates some structural elements from each of these compound classes, a dynamic conformation is likely.

EXAMPLE 6

Preparation of 5,10-diphenyltripyrrane-1,14-dicarboxaldehyde

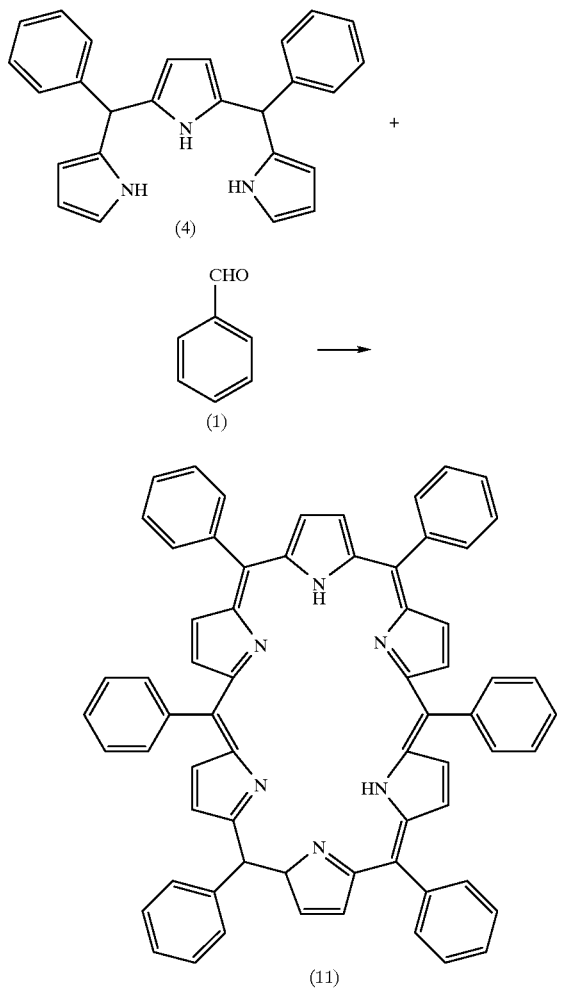

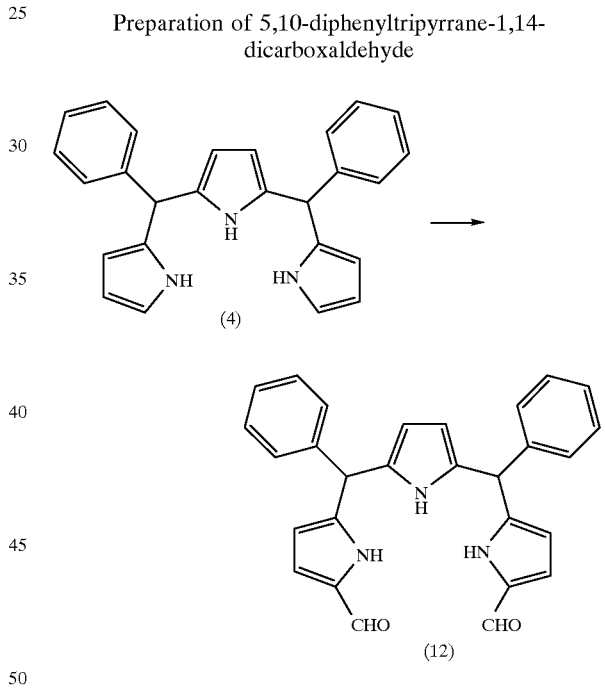

75 mg of the tripyrrane (4) ($2.00 \times 10^{-4}$ mol) and 20 μl of benzaldehyde (1) ($2.0 \times 10^{-4}$ mol) were dissolved in 50 ml of 212 mg of the tripyrrane (4) (56 μmol) were dissolved in 5 ml of DMF, and the solution was stirred under an atmosphere of nitrogen. 71 μl of phosphoryl chloride was injected, and the mixture was heated at 80° C. for one hour. 20 ml of water and 250 mg of potassium carbonate were added, and the mixture was heated for a further 30 minutes at 80° C. The crude mixture was poured into 50 ml of water and extracted three times with 100 ml of ethyl acetate. The combined organic phases were washed with water (5×100 ml), dried over anhydrous sodium sulfate, and evaporated in vacuo. The residue was chromatographed on silica gel, eluting with 1:1 methylene chloride/ethyl acetate containing 1% triethyl amine. 50 mg of analytically pure dialdehyde (12) was obtained by preparative thin layer chromatography (silica gel; 2 mm), eluting with 40% ethyl acetate in methylene chloride containing 1% triethyl amine (21% yield).

Analytical Data:

$^1$H-NMR (CDCl$_3$): δ 9.8 (br s, 2H), 9.0 (s, 2H), 8.65 (br s, 1H), 7.2–7.1 (m, 10H), 6.75 (m, 2H), 6.0 (m, 2H), 5.8 (s, 2H), 5.4 (s, 2H)

HR-MS (EI): Calculated for $^{12}$C$_{28}$H$_{23}$N$_3$O$_2$: 433.1790; found: 433.1794

EXAMPLE 7

Preparation of 18,22-diethyl-17,22-dimethyl-5,10-diphenylpentaphrin (13)

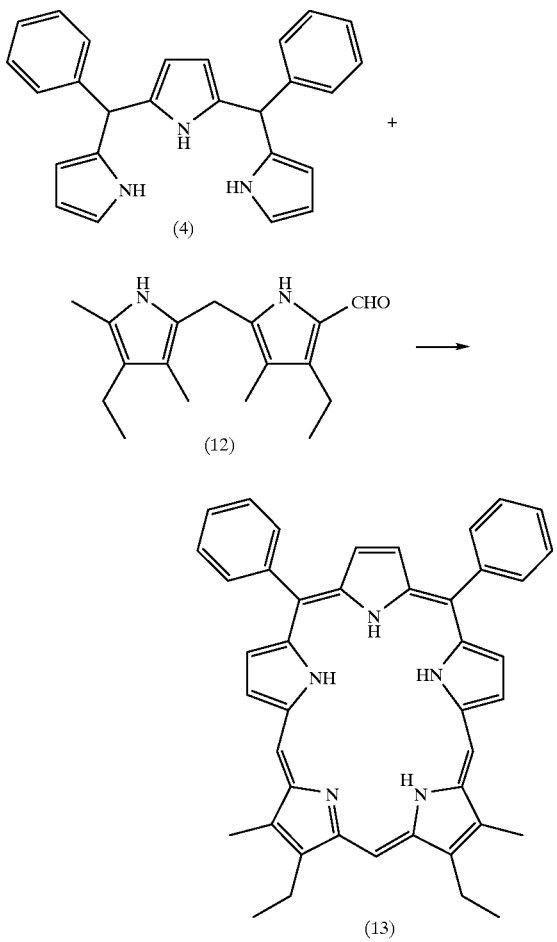

37 mg of the tripyrrane (4) (1.00×10$^{-4}$ mol) and a stoichiometric amount of dipyrromethane dialdehyde (12) are dissolved in 20 ml of ethanol. The mixture is stirred, and 50 mg of p-toluenesulfonic acid are added. After about two hours, three equivalents of dichlorodicyanobenzoquinone ("DDQ") are added. After additional stirring for two hours, the optical spectrum of the mixture was characterized by a strong Soret band at 450 nm and side bands at 528, 90 and 760 nm, all of which are indicative of the formation of the desired pentaphrin in high yields.

We claim:

1. A method for making a compound of Formula I:

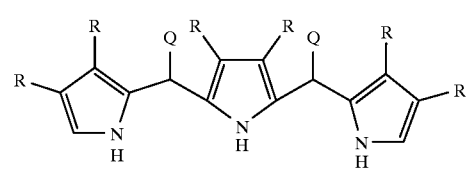

I wherein:
Q represents identical alkyl groups, cycloalkyl groups, aryl groups, or heteroaryl groups; and R represents identical hydrogen, alkyl, alcohol or carbonyl-containing groups; said method comprising the steps of:

(a) reacting a compound of the formula:

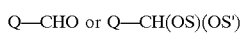

Q—CHO or Q—CH(OS)(OS')

wherein S and S' are independently lower alkyl, an aryl or heteroaryl group containing from 5 to 14 ring atoms, and —(CH$_2$)$_n$— where n=2–4; with a stoichiometric excess of a pyrrole having the formula:

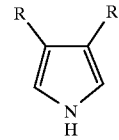

in the presence of a catalytic amount of an acid;

(b) removing the unreacted pyrrole or any other solvents used in (a) by evaporation to form a residue; and (c) treating the residue to remove high molecular weight polymeric materials and the corresponding dipyrromethane by-product, leaving the compound of Formula I.

2. The method of claim 1 wherein an excess molar amount of said pyrrole is used as a solvent.

3. The method of claim 1 wherein an organic solvent other than said pyrrole is used in combination with the excess of said pyrrole to form a mixed solvent.

4. The method of claim 1 wherein the reaction in step (a) thereof takes place at room temperature.

5. The method of claim 1 wherein the unreacted portion of said pyrrole and any other solvents used in step (a) thereof are removed by evaporation in step (b) thereof, under reduced pressure to form a residue.

6. The method of claim 1 wherein the residue is treated in step (c) thereof to remove said polymeric materials chromatographically.

7. The method of claim 1 wherein the residue of step (b) thereof is sublimed in step (c) thereof.

8. The method of claim 7 wherein the subliming step is performed under reduced pressure.

9. A process for making a meso substituted polypyrrolic macrocycle, said process comprising the steps of:

(a) first producing a compound of the formula I, having two terminal pyrrole rings, each with an unsubstituted α-position,

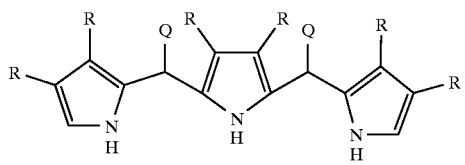

wherein Q represents identical alkyl groups, cycloalkyl groups, aryl groups, or heteroaryl groups; and R represents identical hydrogen, alkyl, alcohol or carbonyl-containing groups, by ($a_1$) reacting a compound of the formula:

Q—CHO or Q—CH(OS)(OS')

wherein S and S' are independently lower alkyl, an aryl or heteroaryl group containing from 5 to 14 ring atoms, and —$(CH_2)_n$— where n=2–4; with a stoichiometric excess of a pyrrole having the formula:

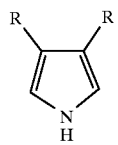

in the presence of a catalytic amount of an acid;

($a_2$) removing the unreacted pyrrole or any other solvents used in (a) to form a residue;

($a_3$) treating the residue to remove any high molecular weight polymeric materials and the corresponding dipyrromethane by-product, thereby leaving the compound of Formula I; and then (b) cyclizing said compound of Formula I with a compound having a formula selected from the group consisting of:
(1) Q'—CHO, wherein Q' is an alkyl group, cycloalkyl group, aryl group, or heteroaryl group;
(2) Q'—CH(OS)(OS'), wherein Q' is an alkyl group, cycloalkyl group, aryl group, or heteroaryl group;

(3)

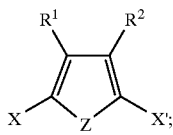

(4)

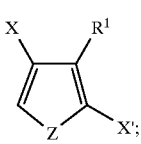

(5)

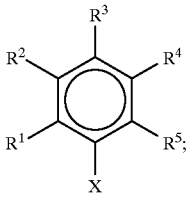

(6)

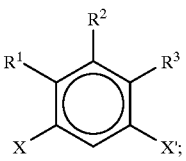

(7)

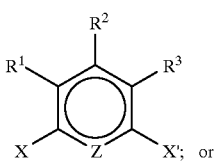

or (8)

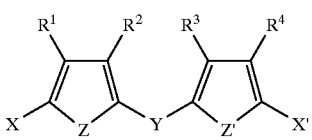

wherein:
S and S' are independently lower alkyl, an aryl group containing from 5 to 14 ring atoms, and —$(CH_2)_n$— where n=2 to 4;

$R^1$–$R^5$ are independently hydrogen, lower alkyl, alcohol or carbonyl-containing groups;

X and X' are groups capable of coupling with the unsubstituted α-positions of the terminal pyrrole rings of the compound of Formula I;

Z and Z' are independently —N—, >NH, —O— or a bivalent sulfur atom; and

Y is a direct link, alkylene, pyrrolylene, furanylene, phenylene, thiophenylene, benzylene, or alkylene-pyrrolene-alkylene, to form a cyclized intermediate; and (c) oxidizing the cyclized intermediate to form the corresponding substituted polypyrrolic macrocycle.

10. The process of claim 9 wherein $R^1$–$R^5$ are selected from the group consisting of hydrogen, methyl, ethyl, n-propyl, i-propyl, n-butyl, tert-butyl, —$C_8H_{17}$, —$OCH_3$, —$O(CH_2CH_2O)_3CH_2CH_3$, —$CH_2OH$, —$(CH_2)_4OH$, —$O(CH_2)_3OH$, —$(CH_2)_2COOH$, —$(CH_2)_2COOCH_3$, and —$(CH_2)_2COOC_2H_5$.

11. The process of claim 9 wherein Y is selected from the group consisting of a direct link, —$CH_2$—, pyrrolene, furanylene, thiophenylene, benzylene and —$CH_2$-pyrrolene-$CH_2$—.

12. The process of claim 9 wherein X and X' have the formula —CHO or —CHR'—L where R' is H, alkyl or aryl, and L is a leaving group.

13. The process of claim 9 wherein X and X' are selected from the group consisting of —CHO, —CH$_2$OH, —CH$_2$NH$_2$, and —CH(Ar)—OH where Ar is aryl having from 5 to 7 ring carbons.

14. The process of claim 9 further comprising, as step (c), purifying the resulting macrocycle.

15. The process of claim 9, wherein said resultant polypyrrolic macrocycle is a 5,10 meso-disubstituted compound.

16. The process of claim 9, wherein the cyclizing in step (a) thereof is performed in the presence of an acid catalyst.

17. The process of claim 9, wherein group Q in Formula I is an aryl or heteroaryl group containing from about 5 to about 14 ring atoms.

18. The process of claim 9, wherein group Q in Formula I is an alkyl group containing from about 1 to about 18 carbon atoms.

19. The process of claim 9, wherein group Q in Formula I is a cycloalkyl group containing from about 5 to 7 carbon atoms.

20. The process of claim 9, wherein group Q in Formula I is aryl or heteroaryl.

21. The process of claim 9 wherein group Q in formula I is phenyl or pyridinyl having one or more substituents selected from the group consisting of halogen, lower alkyl, lower alkoxy, hydroxy, cyano, nitro, or a carboxylic acid.

22. The process of claim 9 wherein group Q in Q—CHO or Q—CH(OS)(OS') is selected from the group consisting of: an aryl or heteroaryl group containing from about 5 to about 14 ring atoms; an alkyl group containing from about 1 to about 18 carbon atoms; and a cycloalkyl group containing from about 5 to 7 carbon atoms.

23. The process of claim 9 wherein R in Formula I thereof is selected from the group consisting of hydrogen, lower alkyl, an alcohol, a carboxy-containing group, and an amide of the formula —CO—NR'R" wherein R' and R" are each independently hydrogen, alkyl, or aryl.

24. The process of claim 9 wherein X and X' have the formula —CHO or —CHR'L where R' is hydrogen, alkyl, or aryl, and L is a leaving group readily lost under conditions of acid catalysis.

* * * * *

UNITED STATES PATENT AND TRADEMARK OFFICE

CERTIFICATE OF CORRECTION

PATENT NO. : 5,919,923

DATED : July 6, 1999

INVENTOR(S) : Christian Bruckner, Ross W. Boyle, and David Dolphin

It is certified that error appears in the above-identified patent and that said Letters Patent is hereby corrected as shown below:

ON THE TITLE PAGE:

**After Line [76], insert --[*] Notice: The term of this patent shall not extend beyond the expiration date of Pat. No. 5,883,246.--**

Signed and Sealed this

Fourteenth Day of March, 2000

*Attest:*

Q. TODD DICKINSON

*Attesting Officer*  Commissioner of Patents and Trademarks